United States Patent
Iizuka et al.

(10) Patent No.: US 8,647,253 B2
(45) Date of Patent: Feb. 11, 2014

(54) SLEEP CONTROL DEVICE AND CONTROL METHOD THEREFOR

(75) Inventors: Hisashi Iizuka, Susono (JP); Hiroki Okamura, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 380 days.

(21) Appl. No.: 12/922,277

(22) PCT Filed: Mar. 6, 2009

(86) PCT No.: PCT/IB2009/005033
§ 371 (c)(1),
(2), (4) Date: Sep. 13, 2010

(87) PCT Pub. No.: WO2009/112944
PCT Pub. Date: Sep. 17, 2009

(65) Prior Publication Data
US 2011/0021866 A1    Jan. 27, 2011

(30) Foreign Application Priority Data

Mar. 11, 2008  (JP) ................................. 2008-061477
Mar. 11, 2008  (JP) ................................. 2008-061535

(51) Int. Cl.
*A61M 21/02*    (2006.01)

(52) U.S. Cl.
USPC .......................................................... 600/26

(58) Field of Classification Search
USPC ................................. 600/26–28; 128/897–899
See application file for complete search history.

(56) References Cited

U.S. PATENT DOCUMENTS

| 3,884,218 A | 5/1975 | Monroe |
| 2005/0283039 A1* | 12/2005 | Cornel .............................. 600/27 |

FOREIGN PATENT DOCUMENTS

| JP | 63097174 A | 4/1988 |
| JP | 07108847 A | 4/1995 |
| JP | 09225034 A | 9/1997 |
| JP | 2003010230 A | 1/2003 |
| JP | 2005021331 A | 1/2005 |
| JP | 2005270439 A | 10/2005 |
| JP | 2005296177 A | 10/2005 |
| JP | 2006516100 | 6/2006 |
| JP | 2007075342 A | 3/2007 |
| JP | 2007098138 A | 4/2007 |
| WO | WO-03039358 A1 | 5/2003 |
| WO | WO-2004032719 A2 | 4/2004 |
| WO | WO-2004075714 A2 | 9/2004 |
| WO | WO-2005055802 A2 | 6/2005 |
| WO | WO-2005089863 A1 | 9/2005 |
| WO | WO-2006092022 A1 | 9/2006 |
| WO | WO 2006092022 A1 * | 9/2006 |
| WO | WO-2007055099 A1 | 5/2007 |

* cited by examiner

*Primary Examiner* — Christine Matthews
*Assistant Examiner* — Joshua D Lannu
(74) *Attorney, Agent, or Firm* — Gifford, Krass, Sprinkle, Anderson & Citkowski, P.C.

(57) ABSTRACT

A drowsiness level detection section detects a drowsiness level of an individual person. A sleep depth level control section controls the sleep depth of the individual person based on the detected drowsiness level. The sleep depth level control section executes a first sleep control, in which the sleep depth level of the individual person is maintained at a predetermined sleep depth level below a maximum sleep depth level, if the detected drowsiness level is equal to or below a predetermined threshold.

28 Claims, 20 Drawing Sheets

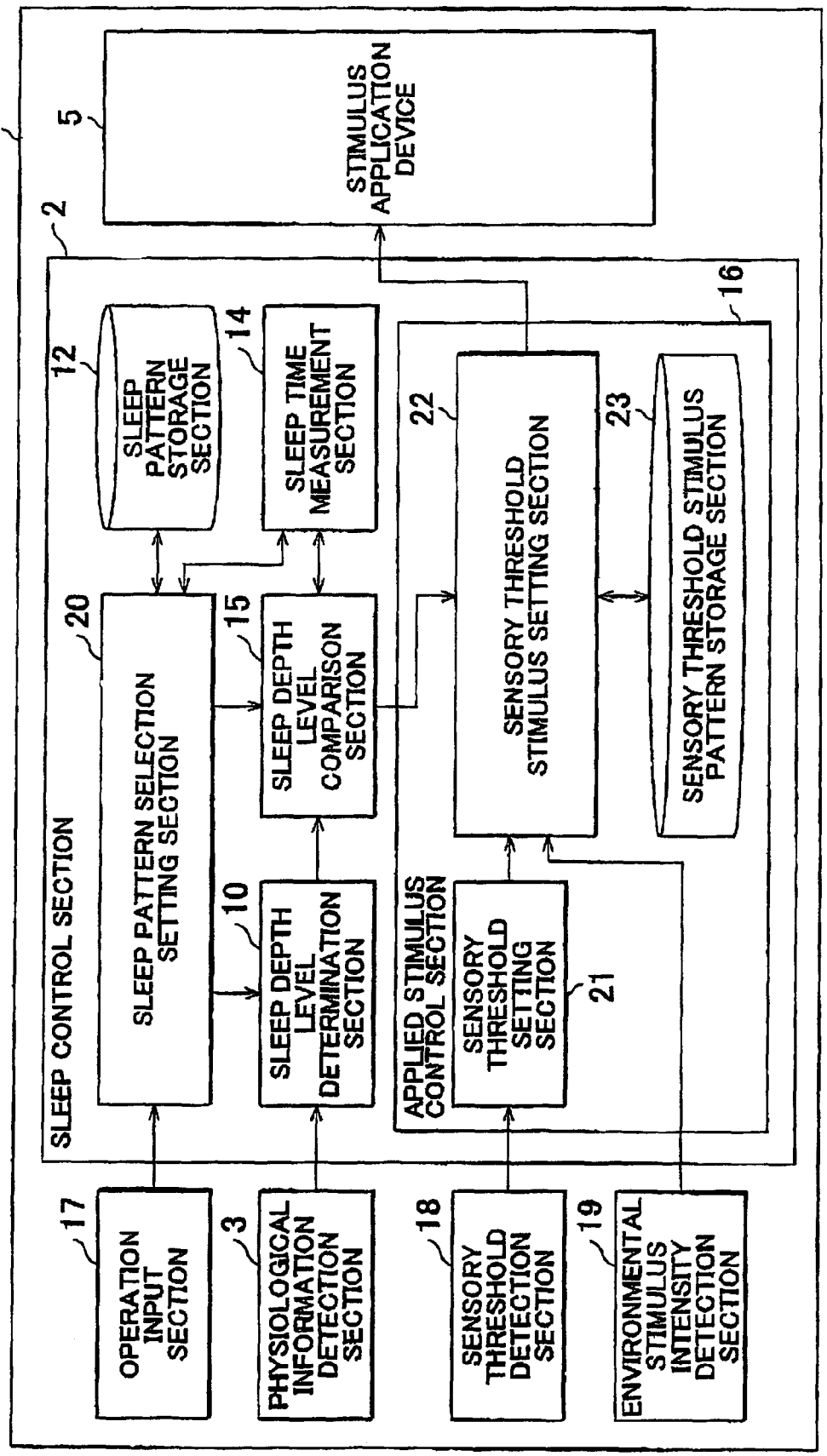

F I G . 10
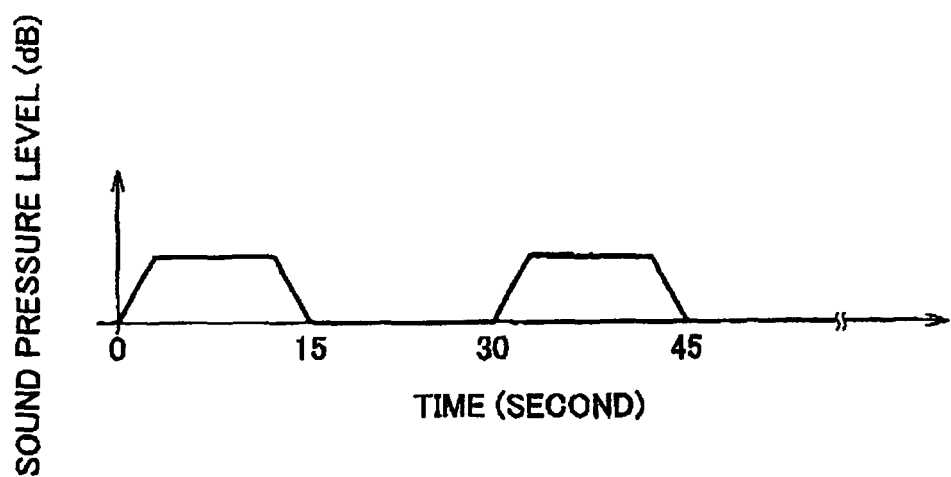

F I G . 12
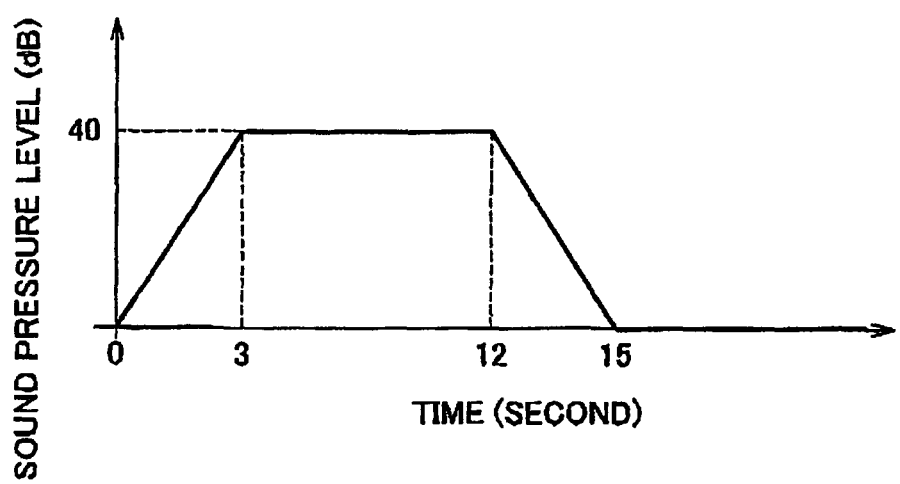

F I G . 17
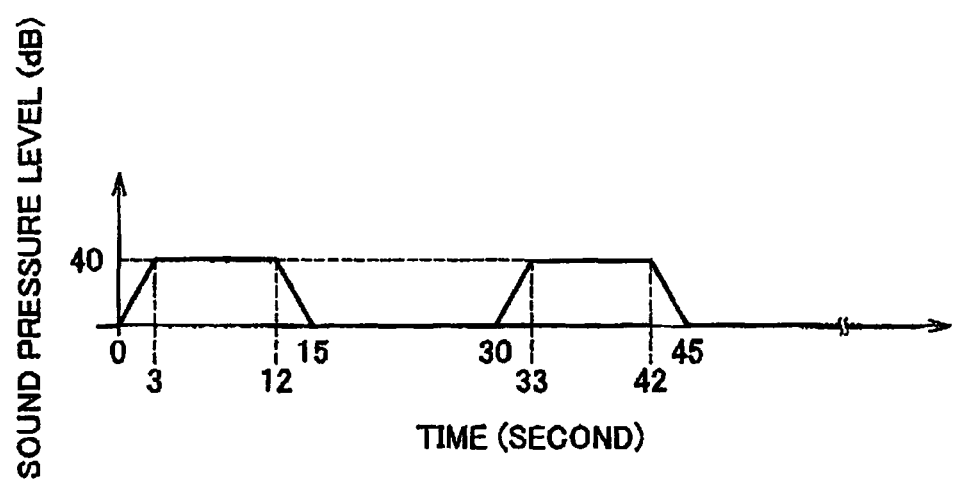

SLEEP CONTROL DEVICE AND CONTROL METHOD THEREFOR

CROSS REFERENCE TO RELATED APPLICATIONS

This application is the U.S. national phase of PCT/IB2009/005033 filed Mar. 6, 2009, which claims priority of Japanese Patent Application Nos. 2008-061477 and 2008-061535 filed Mar. 11, 2008.

BACKGROUND OF THE INVENTION

1. Field of the Invention

The invention relates to a sleep control device that controls the sleep depth level of an individual person, and to a control method for the sleep control device.

2. Description of the Related Art

There has been known a sleep control device that induces a vehicle driver to sleep in the case where the wakefulness level of the driver is lowered to prevent the driver from dozing while driving (see Japanese Patent Application Publication No. 07-108847 (JP-A-07-108847), for example). The sleep control device induces the driver to sleep which utilizes natural sleep rhythms, or wakefulness rhythms, in the case where the wakefulness level is lowered to relieve the drowsiness and recover the fatigue of the driver. The wakefulness rhythms, also referred to as ultradian rhythms, include rapid eye movement (REM) sleep and non-rapid eye movement (NREM) sleep alternated at a frequency of 90 minutes.

The sleep control device can help both relieve the drowsiness and recover the fatigue of an individual person. However, since the individual person is always induced to sleep which utilizes natural sleep rhythms irrespective of the drowsiness level, the individual person may not always feel refreshed when he or she wakes up. Thus, there has been desired a technique allowing the individual person to sleep in such a manner that matches the drowsiness level.

SUMMARY OF THE INVENTION

An object of the invention is to provide a sleep control device that can maintain the sleep depth level of an individual person at a certain level, and a method of controlling the sleep Control device.

A further object of the invention is to provide a sleep control device that can assist an individual person to have appropriate sleep that matches the drowsiness level, and a method of controlling the sleep control device.

Through diligent studies made to solve the aforementioned objects, the inventors focused on both a sleep control scheme to relieve severe drowsiness using the ultradian rhythms discussed above and a nap control scheme to relieve mild drowsiness by keeping the individual person in such light sleep that his or her sleep breaths may be heard for a predetermined time. By further examining the nap control scheme, the inventors discovered that it is effective to maintain sleep at a predetermined depth (sleep depth level) in order to effectively relieve mild drowsiness. Thus, the inventors found that the individual person can be assisted to have appropriate sleep that matches the drowsiness level by performing sleep control so as to maintain the sleep depth level of the individual person based on the sleep pattern that matches the drowsiness level.

Through diligent studies made to achieve the aforementioned objects, the inventors focused on a human sensory threshold for a stimulus. The sensory threshold refers to the minimum intensity of a stimulus that can be sensed by an awakened human. Further consideration of the sensory threshold and the sleep depth level revealed that a human senses a stimulus defined based on the sensory threshold until the sleep depth level reaches a certain level, but hardly senses a stimulus defined based on the sensory threshold after the sleep depth level exceeds the certain level. Thus, the inventors found that the sleep depth level of the individual person can be maintained at the certain level by utilizing a sensory threshold stimulus having an intensity defined based on the human sensory threshold.

A first aspect of the invention provides a sleep control device including a drowsiness level detection section that detects a drowsiness level of an individual person, and a sleep depth level control section that controls a sleep depth level of the individual person based on the drowsiness level detected by the drowsiness level detection section. The sleep depth level control section executes a first sleep control in which the sleep depth level of the individual person is maintained at a predetermined sleep depth level below a maximum sleep depth level if the drowsiness level detected by the drowsiness level detection section is equal to or below a predetermined threshold.

According to the sleep control device, the individual person having mild drowsiness can be kept in light sleep by the sleep depth level control section which executes the first sleep control in which the sleep depth level of the individual person is maintained at a predetermined sleep depth level below a maximum sleep depth level if the detected drowsiness level is equal to or below a predetermined threshold. By keeping the individual person in light sleep in this way, it is possible to relieve mild drowsiness of the individual person effectively in a short time. In addition, it is possible to suppress deterioration in the responsiveness of the individual person after being awakened by not permitting the sleep depth level to reach the maximum sleep depth level.

In the sleep control device in accordance with the first aspect, the sleep depth level control section may execute a second sleep control in which the sleep depth level of the individual person is maintained at a level that is higher than the predetermined sleep depth level at which the sleep depth level is maintained during the first sleep control, utilizing natural sleep rhythms of the individual person if the drowsiness level detected by the drowsiness level detection section exceeds a predetermined threshold. The individual person having severe drowsiness can be kept in deep sleep by executing the second sleep control. This promotes fatigue recovery etc., effectively relieving severe drowsiness of the individual person.

The sleep control device in accordance with the first aspect may include a physiological information detection section that detects physiological information of the individual person, and a sleep depth level determination section that determines the sleep depth level of the individual person based on the physiological information detected by the physiological information detection section. With the physiological information detection section, it is possible to determine the sleep depth level of the individual person based on the physiological information such as the heart rate of the individual person, for example.

In the sleep control device in accordance with the first aspect of the invention, the sleep depth level control section may apply an awakening stimulus to the individual person in order to decrease the sleep depth level if the determined sleep depth level by the sleep depth level determination section is higher than the predetermined sleep depth level during the first sleep control. In addition, the sleep depth level control section may apply a sleep-inducing stimulus to the individual person in order to increase the sleep depth level if the determined sleep depth level by the sleep depth level determination section is below the predetermined sleep depth level during the first sleep control. By applying the awakening stimulus and the sleep-inducing stimulus to the individual person in the first sleep control, the sleep depth level of the individual person can be maintained at the predetermined sleep depth level more reliably.

In the sleep control device in accordance with the first aspect of the invention, the sleep depth level control section may apply asleep-inducing stimulus to the individual person in order to increase the sleep depth level until the determined sleep depth level by the sleep depth level determination section reaches the maximum sleep depth level during the second sleep control. This enables the individual person to have deep sleep immediately.

In the sleep control device in accordance with the first aspect of the invention, the sleep depth level control section may apply an awakening stimulus to the individual person in order to awaken the individual person when the determined sleep depth level decreases to a predetermined sleep depth level after reaching the maximum sleep depth level. By temporarily introducing the individual person into deep sleep using natural sleep rhythms and then promptly awakening the individual person from the predetermined light sleep depth level, it is possible to suppress deterioration in the responsiveness of the individual person compared to the case where the individual person is gradually awakened using natural sleep rhythms.

In the sleep control device in accordance with the first aspect of the invention, the sleep depth level control section may set a time period over which the first sleep control is executed according to the detected drowsiness level. This allows providing further effective sleep assistance according to the degree of the drowsiness level.

In the sleep control device in accordance with the first aspect of the invention, the sleep depth level control section may apply an awakening stimulus to the individual person in order to awaken the individual person after the set time elapses during the first sleep control.

In the sleep control device in accordance with the first aspect of the invention, the drowsiness level detection section may detect the drowsiness level of the individual person based on the detected physiological information. With the physiological information detection section, it is possible to determine the current drowsiness level of the individual person based on the physiological information such as the number of blinks and the heart rate of the individual person.

A method of controlling the sleep control device in accordance with the first aspect of the invention includes detecting a current drowsiness level of an individual person, and executing first sleep control in which a sleep depth level of the individual person is maintained at a predetermined sleep depth level below a maximum sleep depth level, if the drowsiness level is equal to or below a predetermined threshold.

The sleep control device in accordance with the first aspect of the invention can maintain the sleep depth level of the individual person at a certain level, and assist the individual person to have appropriate sleep that matches the drowsiness level of the individual person.

A second aspect of the invention provides a sleep control device including a sleep depth level determination section that determines a current sleep depth level of an individual person, a sleep depth level comparison section that compares the determined current sleep depth level with a target sleep depth level, and a stimulus application section that applies to the individual person a sensory threshold stimulus having an intensity defined based on a human sensory threshold if the sleep depth level comparison section determines that the current sleep depth level reaches the target sleep depth level.

The sleep control device in accordance with the second aspect of the invention applies the sensory threshold stimulus having an intensity defined based on the human sensory threshold to the individual person if it is determined that the current sleep depth level of the individual person reaches the target sleep depth level. By applying the sensory threshold stimulus in this way, the sleep depth level of the driver can be maintained at the predetermined sleep depth level. This allows the individual person to feel significantly refreshed when he or she wakes up even after short hours of sleep such as napping.

The sleep control device in accordance with the second aspect of the invention may further include a sensory threshold detection section that detects an intensity defined based on a sensory threshold of the individual person, and an environmental stimulus intensity detection section that detects an intensity of a stimulus that the individual person receives from a surrounding environment. The stimulus application section may apply a stimulus to the individual person with an intensity obtained by subtracting the detected environmental intensity from the detected sensory threshold intensity, as the sensory threshold stimulus. By applying the sensory threshold stimulus at the intensity obtained by subtracting the detected environmental intensity that the driver receives from the surrounding environment from the detected sensory threshold intensity, the sleep depth level of the driver can be maintained at the predetermined sleep depth level further reliably.

In the sleep control device in accordance with the second aspect of the invention, the stimulus application section may apply the sensory threshold stimulus to the individual person intermittently. If the intensity of a stimulus is constant, a human may be adapted to the stimulus, and thus the responsiveness of the human to the stimulus may deteriorate. Thus, by intermittently applying the sensory threshold stimulus to the individual person, the sleep depth level of the individual person can be maintained at the predetermined sleep depth level further reliably.

In the sleep control device in accordance with the second aspect of the invention, the stimulus application section may apply the sensory threshold stimulus to the individual person so that a change in the intensity of the sensory threshold stimulus per unit time is $dV/dt$ or less, in which a human intensity discrimination threshold for the sensory threshold stimulus is defined as $dV$ and a human time discrimination threshold for the sensory threshold stimulus is defined as $dt$. A rapid change in the stimulus intensity may awaken the individual person. Thus, by adjusting changes in the intensity of the sensory threshold stimulus based on the human discrimination threshold, the sleep depth level of the individual person can be maintained at the predetermined sleep depth level further reliably.

The sleep control device in accordance with the second aspect may further include a physiological information detection section that detects physiological information of the individual person. The sleep depth level determination section may detect the current sleep depth level of the individual person based on the detected physiological information. With the physiological information detection section, it is possible to determine the current sleep depth level of the individual person precisely based on the detected physiological information such as the heart rate of the individual person.

A control method for the sleep control device in accordance with the second aspect of the invention includes determining a current sleep depth level of a individual person, comparing the current sleep depth level with a target sleep depth level to determine whether the current sleep depth level reaches the target sleep depth level, and applying a sensory threshold stimulus to the individual person. The sensory threshold stimulus includes an intensity defined based on a human sensory threshold.

The sleep control device in accordance with the second aspect of the invention can maintain the sleep depth level of the individual person appropriately at a certain level.

The invention is not limited to the first aspect and the second aspect. The first aspect and the second aspect may be implemented separately, or may be implemented in combination.

BRIEF DESCRIPTION OF THE DRAWINGS

The features, advantages, and technical and industrial significance of this invention will be described in the following detailed description of example embodiments of the invention with reference to the accompanying drawings, in which like numerals denote like elements, and wherein:

FIG. 9 shows the configuration of a sleep control device in accordance with a second embodiment of the invention;

FIG. 10 shows a sensory threshold stimulus pattern for use by the sleep control device in accordance with the second embodiment of the invention;

FIG. 12 shows an example of a sensory threshold stimulus pattern;

FIG. 17 shows a sensory threshold stimulus pattern with a change rate of the discrimination threshold or less for use in a number-of-awakenings test;

DETAILED DESCRIPTION OF EMBODIMENTS

Hereinafter, a detailed description will be made of embodiments of a sleep control device in accordance with the invention with reference to the drawings.

Figure 1:
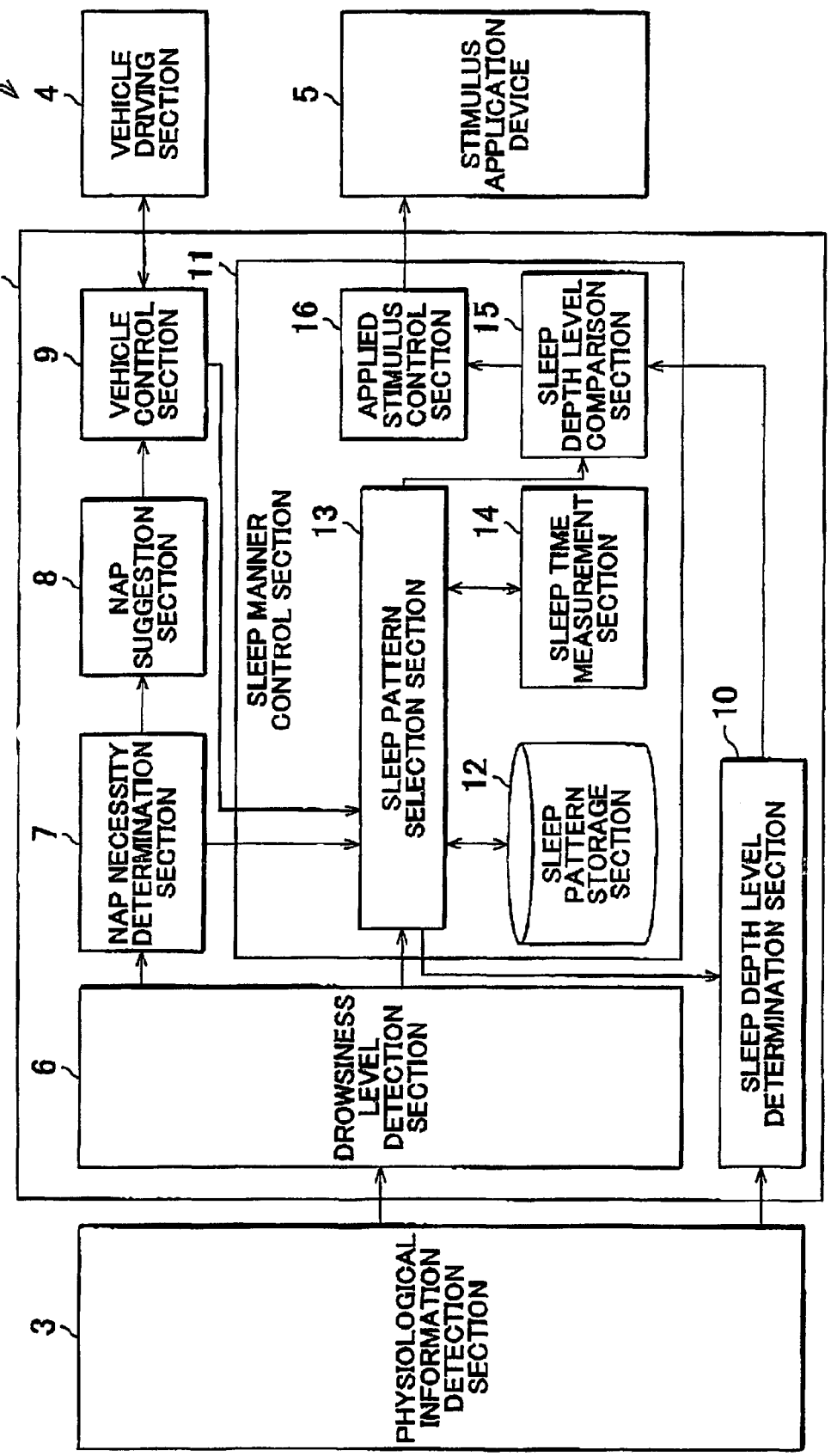
FIG. 1 shows the configuration of a sleep control device in accordance with a first embodiment of the invention.

FIG. 1 shows the configuration of a sleep control device in accordance with a first embodiment of the invention. A sleep control device 1 shown in FIG. 1 is installed in vehicles such as automobiles. The sleep control device 1 assists a driver (individual person) of a vehicle to have appropriate sleep that matches the drowsiness level of the driver after parking the vehicle at a predetermined location when the driver is feeling drowsy while driving. The sleep control device 1 includes an electronic control unit 2 that executes overall control of the sleep control device 1.

A physiological information detection section 3 that detects physiological information of the driver is connected to the control unit 2. The physiological information detection section 3 detects physiological information such as the number of blinks and the heart rate of the driver. The physiological information detection section 3 may be constituted by an image sensor and an image processing section that measure the number of blinks, for example. The image sensor may be attached to the front panel of the vehicle to capture a face of the driver, for example. The image processing section may process a plurality of facial images of the driver captured by the image sensor to measure the number of blinks in a certain time.

Another example of the physiological information detection section 3 is a heart rate measurement sensor that measures the heart rate, for example. The heart rate measurement sensor may be built in the back rest of a driver's seat to measure the heart rate of the driver, for example. When an engine of the vehicle is started, the physiological information detection section 3 starts detecting various physiological information. The physiological information detection section 3 outputs the various detected physiological information to the control unit 3.

A vehicle driving section 4 and a stimulus application device 5 are also connected to the control unit 2. The vehicle driving section 4 transmits power of the engine to wheels to move the vehicle in a predetermined direction. The vehicle driving section 4 guides the vehicle to a predetermined location based on a command signal received from the control unit 2.

The stimulus application device 5 applies a physical stimulus to the driver. The stimulus application device 5 may be a speaker that applies an auditory stimulus by reproducing sound, for example. The speaker may be built in the head rest of the driver's seat, for example. Another example of the stimulus application device 5 is a light emitter that applies a visual stimulus by emitting light, for example. The light emitter may be attached to the front panel, for example.

The control unit 2 includes a drowsiness level detection section 6 that detects the current drowsiness level of the driver, a nap necessity determination section 7 that determines the necessity of a nap, a nap suggestion section 8 that suggests taking a nap to the driver, a vehicle control section 9 that performs control so as to guide the vehicle to a predetermined parking location, a sleep depth level determination section 10 that determines the sleep depth level of the driver being asleep (hereinafter referred to as "current sleep depth level"), and a sleep manner control section (sleep depth level control section) 11 that controls the sleep pattern (sleep manner) of the driver based on the drowsiness level.

Figure 2:
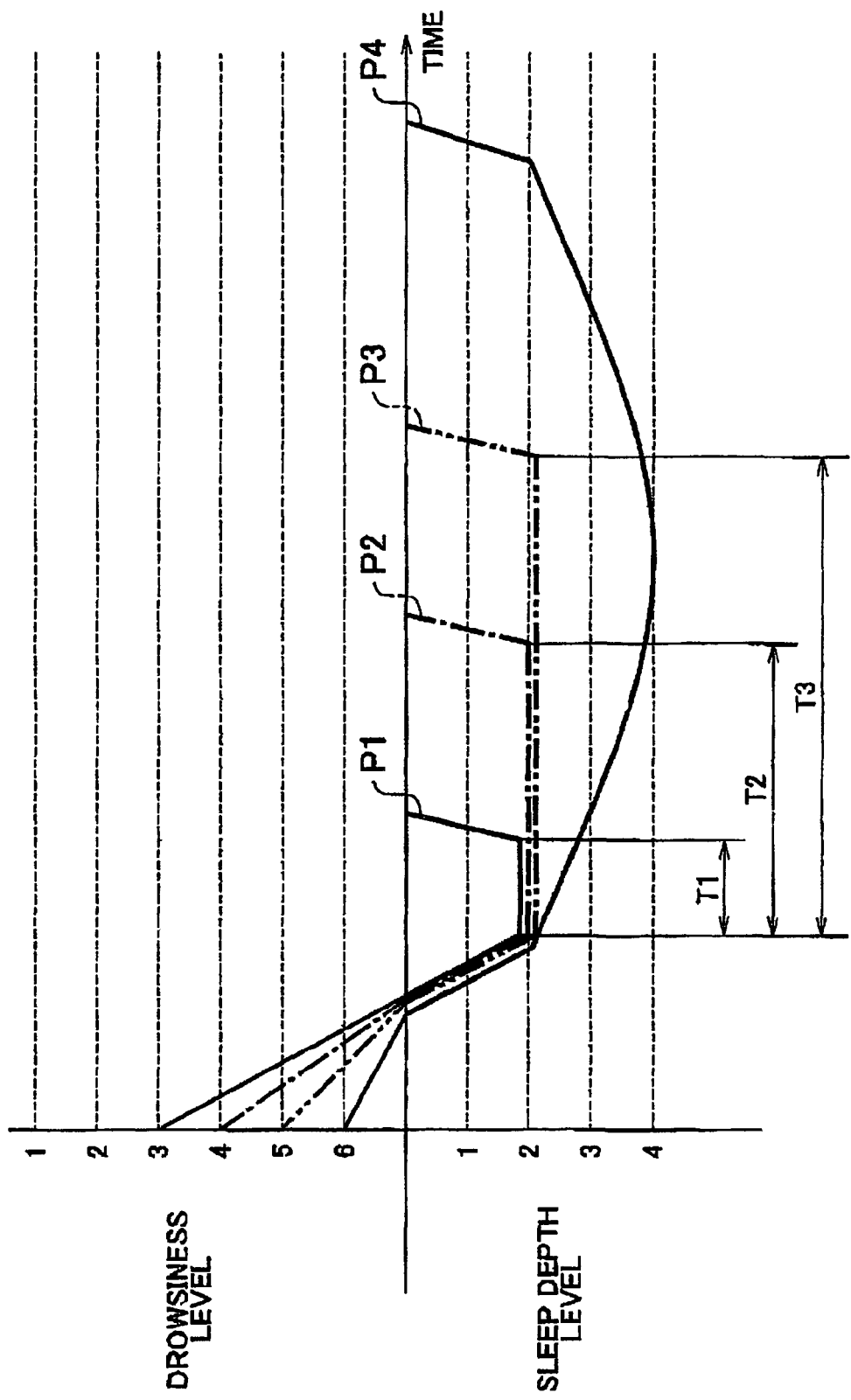
FIG. 2 shows sleep patterns P1 to P4.

The drowsiness level detection section 6 detects the drowsiness level of the driver based on the various physiological information detected by the physiological information detection section 3. The drowsiness level detection section 6 detects the drowsiness level according to the physiological information detected by the physiological information detection section 3, such as the number of blinks and the heart rate, to output the detected drowsiness level to the nap necessity determination section 7 and the sleep manner control section 11. As shown in FIG. 2, the drowsiness level is classified into six levels according to the degree of the drowsiness, namely from level 1 which corresponds to mild drowsiness to level 6 which corresponds to severe drowsiness. In the first embodiment, the drowsiness levels 1 and 2 are defined as extremely mild drowsiness, the drowsiness levels 3 to 5 are defined as mild drowsiness, and the drowsiness level 6 is defined as severe drowsiness which requires fatigue recovery.

The nap necessity determination section 7 determines whether or not a nap is necessary for the driver. In the case where the drowsiness level detection section 6 detects the drowsiness levels 3 to 6, the nap necessity determination section 7 generates information that indicates that a nap is necessary. In the case where the drowsiness level detection section 6 detects the drowsiness levels 1 and 2, on the other hand, the nap necessity determination section 7 generates information that indicates that a nap is necessary or is not necessary. The nap necessity determination section 7 outputs the information that indicates that a nap is necessary or is not necessary to the nap suggestion section 8 and the sleep manner control section 11.

The nap suggestion section 8 informs the driver that the sleep control device 1 starts sleep assistance. When the information that indicates that a nap is necessary is received from the nap necessity determination section 7, the nap suggestion section 8 informs the driver through a speaker of the vehicle that the sleep control device 1 starts sleep assistance. After informing, the nap suggestion section 8 generates an information termination signal and outputs the signal to the vehicle control section 9.

The vehicle control section 9 controls the vehicle driving section 4. A global positioning system (GPS) device (not shown) may be connected to the vehicle control section 9 so that vehicle position information can be obtained, for example. When the information termination signal is received from the nap suggestion section 8, the vehicle control section 9 executes control so as to guide the vehicle to a safe location, such as a parking space, that is the closest to the location at which the vehicle is running based on the vehicle position information obtained from the GPS device. When it is confirmed that the GPS device has finished guiding the vehicle and a parking brake has been actuated, the vehicle control section 9 generates a vehicle stop signal and outputs the signal to the sleep manner control section 11.

The sleep depth level determination section 10 determines the current sleep depth level of the driver. After a sleep manner control start signal is received from the sleep manner control section 11, the sleep depth level determination section 10 determines the current sleep depth level of the driver based on the heart rate detected by the physiological information detection section 3. The sleep depth level determination section 10 outputs the determined current sleep depth level to the sleep manner control section 11.

The sleep manner control section 11 executes control so as to provide the driver with a sleep pattern that matches the drowsiness level. The sleep manner control section 11 includes a sleep pattern storage section 12 that stores a plurality of sleep patterns, a sleep pattern selection section 13 that selects a sleep pattern in accordance with the drowsiness level, a sleep time measurement section 14 that measures the elapsed time of the selected sleep pattern, a sleep depth level comparison section 15 that compares the current sleep depth level with the sleep depth level in accordance with the selected sleep pattern, and an applied stimulus control section 16 that applies a stimulus to the driver based on the comparison results by the sleep depth level comparison section 15.

The sleep pattern storage section 12 stores a plurality of sleep patterns P1 to P4 that match respective drowsiness levels. As shown in FIG. 2, the sleep patterns P1 to P4 are divided into the sleep patterns P1 to P3 respectively corresponding to the drowsiness levels 3 to 5 as mild drowsiness and the sleep pattern P4 corresponding to the drowsiness level 6 as severe drowsiness.

Figure 3:
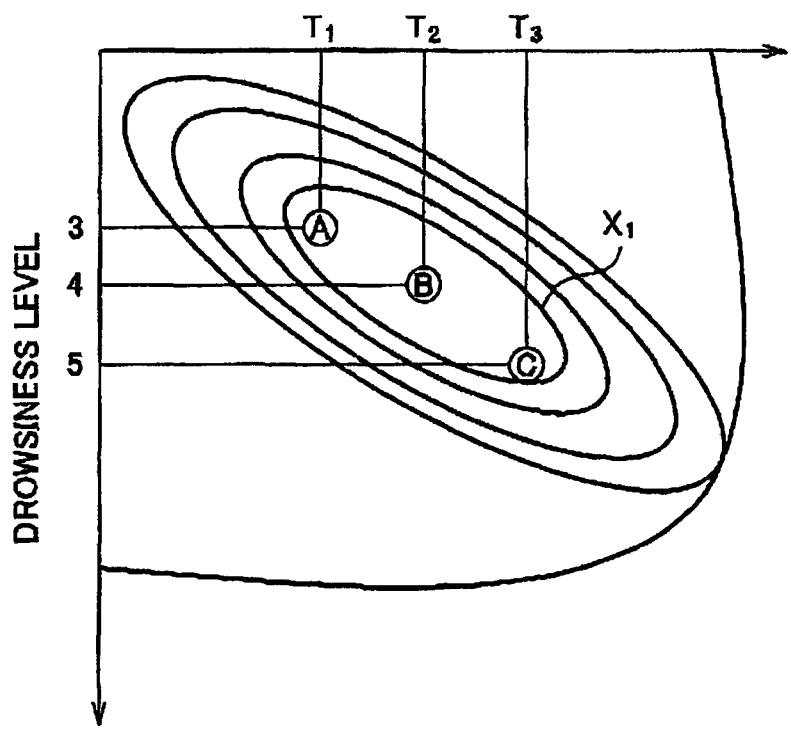
FIG. 3 shows the relationship between the drowsiness level and the duration time in the sleep patterns P1 to P3.

In the sleep patterns P1 to P3, the driver is maintained at the sleep depth level 2, at which his or her sleep breaths may be heard, for a certain time. That is, as shown in FIG. 2, the sleep pattern P1 corresponds to the drowsiness level 3, and in the sleep pattern P1, the driver is maintained at the sleep depth level 2 for a time T1 of about 5 minutes, for example. The sleep pattern P2 corresponds to the drowsiness level 4, and in the sleep pattern P2, the driver is maintained at the sleep depth level 2 for a time T2 of about 10 minutes, for example. The sleep pattern P3 corresponds to the drowsiness level 5, and in the sleep pattern P3, the driver is maintained at the sleep depth level 2 for a time T3 of about 30 minutes, for example. In other words, the duration time is longer as the drowsiness level is higher in the sleep patterns P1 to P3. FIG. 3 shows the relationship between the sleep depth level 2 and the optimum duration times. As shown in FIG. 3, the optimum duration times for the drowsiness levels 3 to 5 are represented in an innermost circle X1. The duration times are set within the innermost circle X1.

In contrast, the sleep pattern P4 utilizes natural sleep rhythms. In the sleep pattern P4, as shown in FIG. 2, the sleep depth level of the driver is increased to the sleep depth level 4 utilizing natural sleep rhythms, and maintained at the sleep depth level 4 for a while. When the sleep depth level lowers to the sleep depth level 2 after the sleep depth level 4 is maintained for a while, the driver is awakened.

The sleep pattern selection section 13 selects one of the sleep patterns P1 to P4 stored in the sleep pattern storage section 12 that matches the drowsiness level detected by the drowsiness level detection section 6, to set the selected sleep pattern as the sleep manner in which sleep control should be performed. Information about the sleep pattern set by the sleep pattern selection section 13 is output to the sleep time measurement section 14 and the sleep depth level comparison section 15.

The sleep time measurement section 14 measures a sleep time, which is an elapsed time from the start of the sleep pattern selected by the sleep pattern selection section 13. The sleep time measurement section 14 outputs the measured sleep time to the sleep pattern selection section 13. The sleep depth level comparison section 15 compares the current sleep depth level determined by the sleep depth level determination section 10 with the sleep depth level in accordance with the sleep pattern selected by the sleep pattern selection section 13 (hereinafter referred to as "target sleep depth level"), to output a comparison signal indicating the obtained difference between the levels to the applied stimulus control section 16.

When the comparison signal is received from the sleep depth level comparison section 15, the applied stimulus control section 16 executes control so as to drive the stimulus application device 5 to apply one of an awakening stimulus, a maintaining stimulus, and a sleep-inducing stimulus based on the comparison signal. The applied stimulus control section 16 outputs an awakening stimulus application signal, a maintaining stimulus application signal, or a sleep-inducing stimulus application signal to the stimulus application device 5 based on the comparison signal received from the sleep depth level comparison section 15.

Figure 4:
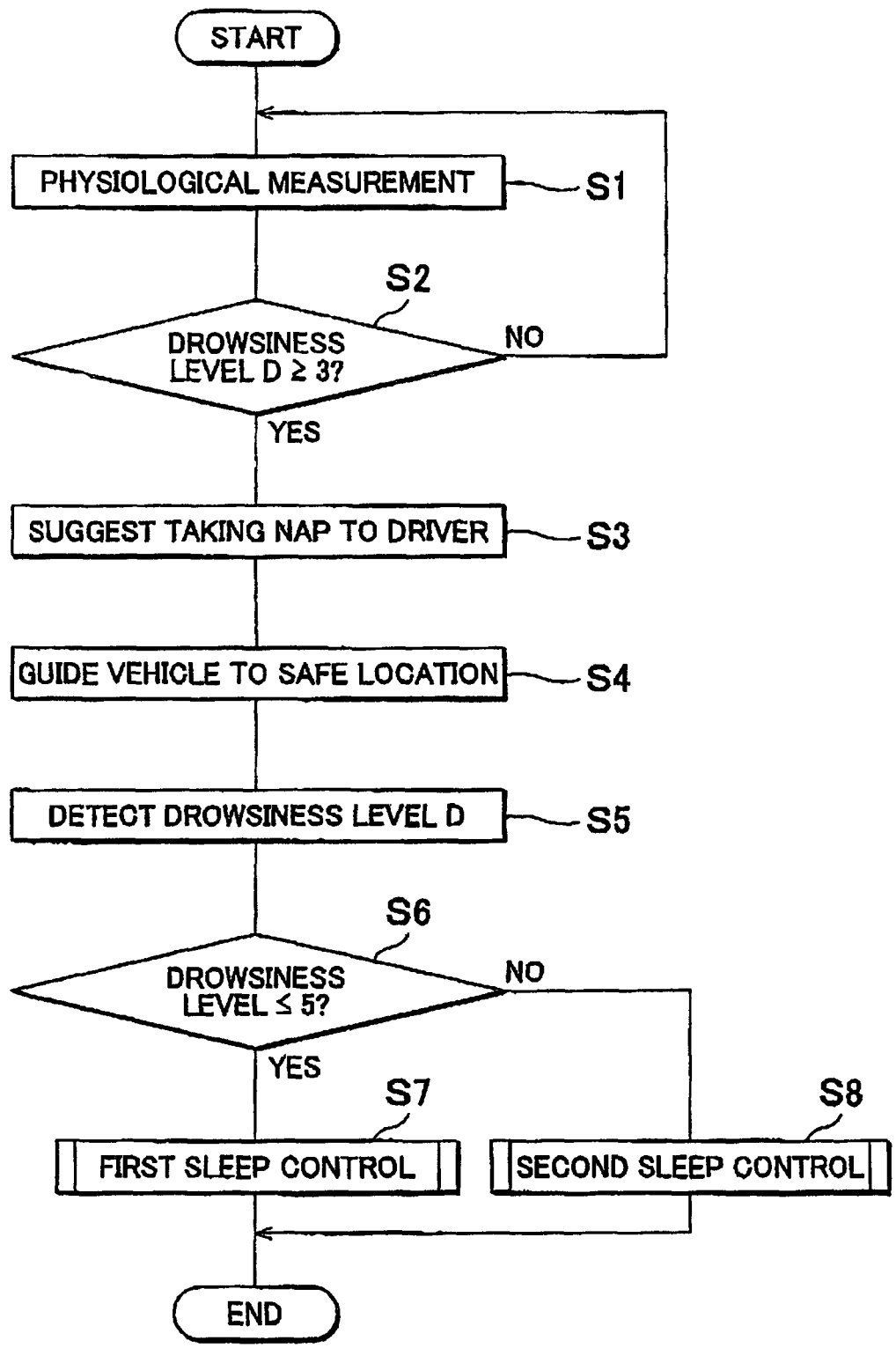
FIG. 4 is a flowchart showing the operation of the sleep control device in accordance with the first embodiment shown in FIG. 1.
Figure 5:
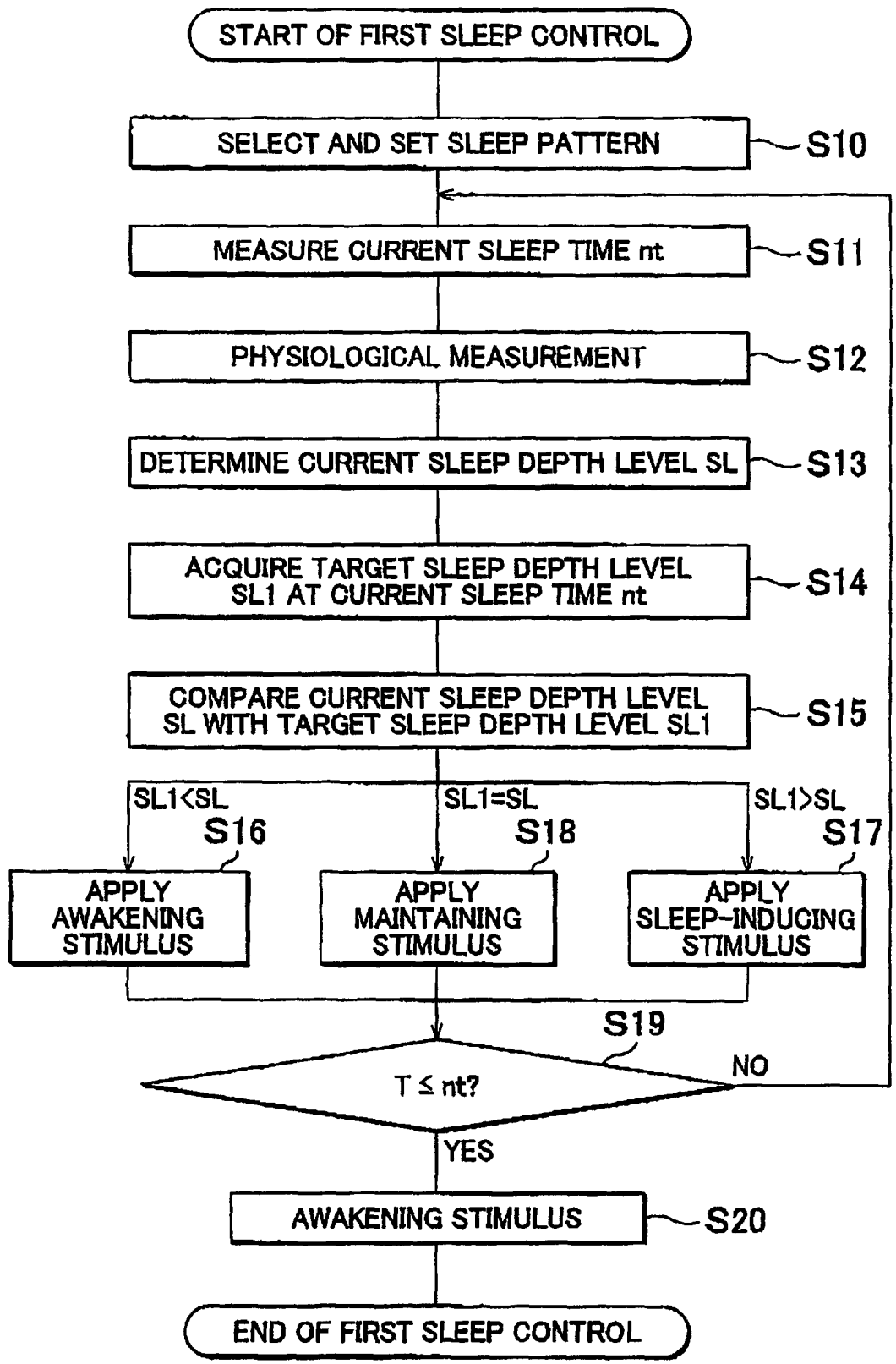
FIG. 5 is a flowchart showing the operation of first sleep control.
Figure 6:
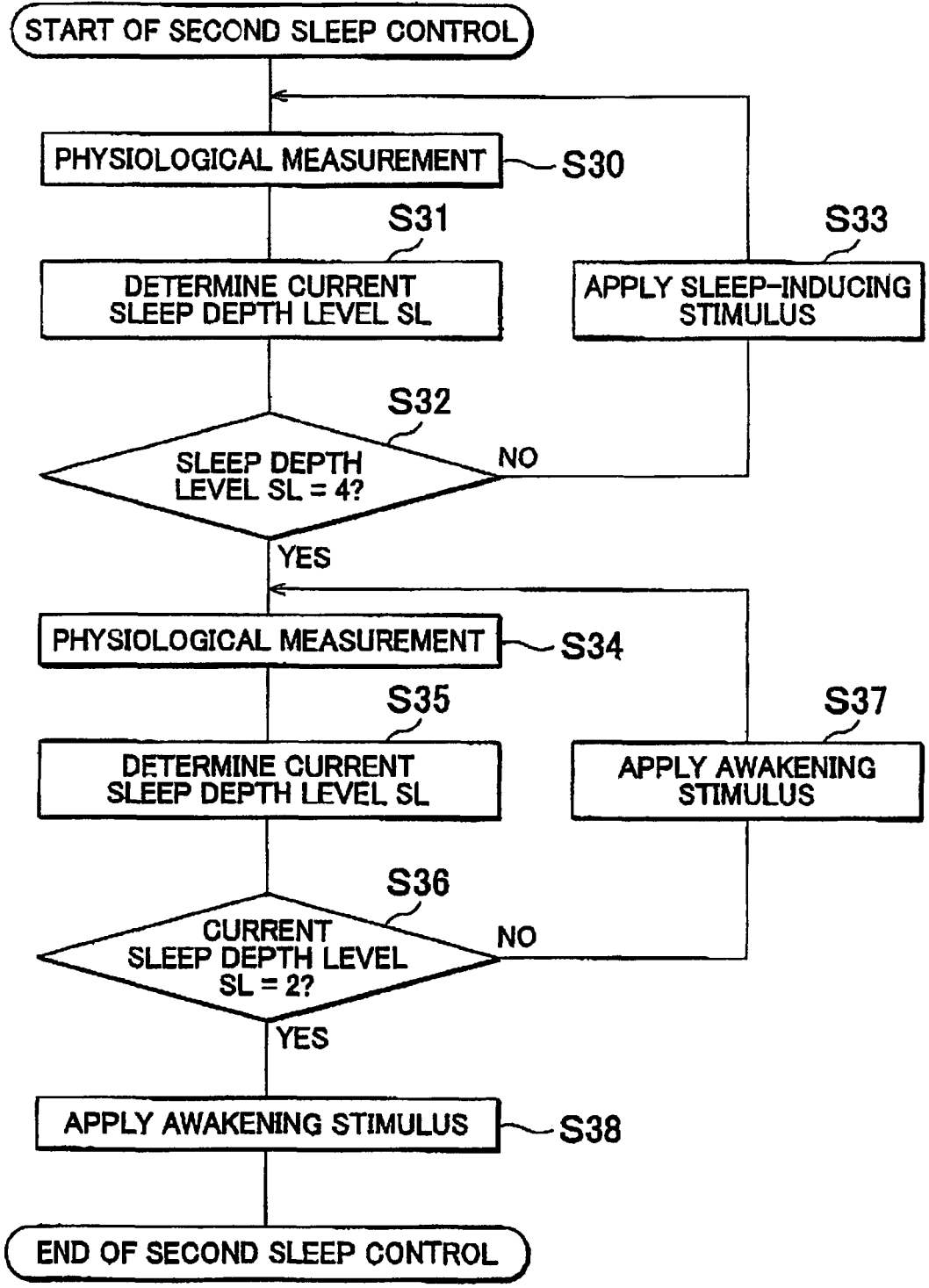
FIG. 6 is a flowchart showing the operation of second sleep control.

Now, a description will be made of the operation of the aforementioned sleep control device 1 with reference to the flowcharts shown in FIGS. 4 to 6. The sequence of control processes described below is executed by the control unit 2 repeatedly at a predetermined frequency.

First, in step S1, a physiological measurement process is executed. In the process, various sensors of the physiological information detection section 3 detect the number of blinks, the heart rate, etc., of the driver to measure the physiological state of the driver.

Next, the drowsiness level detection section 6 detects a drowsiness level D of the driver based on the physiological information measured in step S1, and the nap necessity determination section 7 determines whether or not the driver is feeling drowsy (S2). In step S2, it is determined that the driver is feeling drowsy in the case where the drowsiness level D of the driver is 3 or higher. In the case where the drowsiness level D is not 3 or higher in step S2, the process returns to step S1 to repeat the physiological measurement.

Subsequently, in the case where the drowsiness level D is detected to be 3 or higher in step S2, the nap suggestion section 8 sends the driver a nap suggestion message through the speaker (S3). Then, the process proceeds to step S4, where the vehicle control section 9 executes control so as to drive the vehicle driving section 4 in order to guide the vehicle of the driver to a safe location, at which the vehicle can be parked, based on GPS information or the like. When the vehicle is guided to a safe location, the process proceeds to step S5, where the drowsiness level detection section 6 detects a drowsiness level D of the driver again.

Subsequently, the sleep pattern selection section 13 determines whether the drowsiness level D detected in step S5 is 3 to 5 which corresponds to mild drowsiness, or 6 which corresponds to severe drowsiness (S6). In the case where the determination result of step S6 indicates that the drowsiness level D is 3 to 5a, a first sleep control is executed in which the sleep depth level is maintained at the sleep depth level 2, which is lower than the sleep depth level 4 or the maximum level, for a certain time (S7). In the first sleep control executed in step S7, the sleep pattern selection section 13 invokes, and sets, one of the sleep patterns P1 to P3 from the sleep pattern storage section 12.

In contrast, in the case where the determination result of step S6 indicates that the drowsiness level D is 6, a second sleep control is executed in which the sleep depth level is kept at the sleep depth level 4 utilizing a natural sleep pattern (S8). In the second sleep control executed in step S8, the sleep pattern selection section 13 invokes, and sets, the sleep pattern P4 from the sleep pattern storage section 12.

Now, a detailed description will be made of the first sleep control with reference to FIG. 5. The sequence of control processes of the first sleep control described below is executed by the control unit 2 repeatedly for a predetermined time.

First, in step S10, the sleep pattern selection section 13 selects, and sets, one of the sleep patterns P1 to P3 that matches the drowsiness level D detected by the drowsiness level detection section 6. By setting the sleep pattern, a sleep duration time T in accordance with the selected sleep pattern and a target sleep depth level SL1 at a predetermined time are set.

After the sleep pattern is set in step S10, a first sleep control in accordance with the set sleep pattern is started, and the sleep time measurement section 14 measures a current sleep time nt, which is equivalent to the elapsed time (S11). Subsequently, the physiological information detection section 3 executes physiological measurement again (S12). Then, the sleep depth level determination section 10 determines the current sleep depth level SL of the driver based on the physiological information from the physiological information detection section 3 such as the heart rate (S13).

After the current sleep depth level SL of the driver is determined in step S13, a target sleep depth level SL1 in accordance with the selected sleep pattern at the current sleep time nt is acquired (S14). Then, the sleep depth level comparison section 15 compares the current sleep depth level SL determined in step S13 with the target sleep depth level SL1 acquired in step S14 (S15).

In the case where the comparison result of step S15 indicates that the current sleep depth level SL is higher than the target sleep depth level SL1, that is, the driver is sleeping at a greater depth than the target depth, the applied stimulus control section 16 actuates the stimulus application device 5 to apply to the driver an awakening stimulus which lowers the sleep depth level of the driver (S16). The awakening stimulus may be suitably selected from a visual stimulus such as flash light emitted by a light emitting device, an auditory stimulus such as music reproduced at a sound pressure level exceeding a sensory threshold (about 60 to 80 dB of white noise, for example), etc.

In the case where the comparison result of step S15 indicates that the current sleep depth level SL is lower than the target sleep depth level SL1, that is, the driver is sleeping at a shallower depth than the target depth, the applied stimulus control section 16 actuates the stimulus application device 5 to apply to the driver a sleep-inducing stimulus which increases the sleep depth level of the driver (S17). The sleep-inducing stimulus may be suitably selected from a perceptive stimulus such as adjusting the room temperature suitably for sleep, a tactile stimulus by massage, an auditory stimulus such as reproducing music suitable for sleep, etc.

Figure 7:
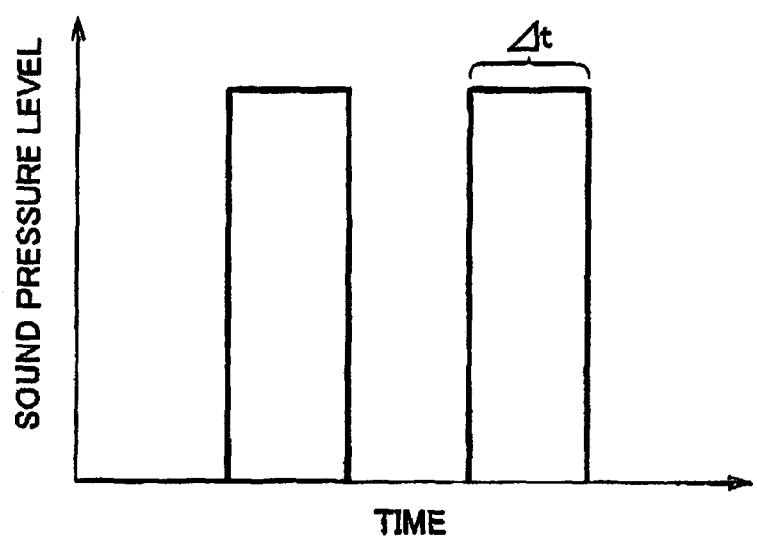
FIG. 7 shows an example of a maintaining stimulus.
Figure 8A:
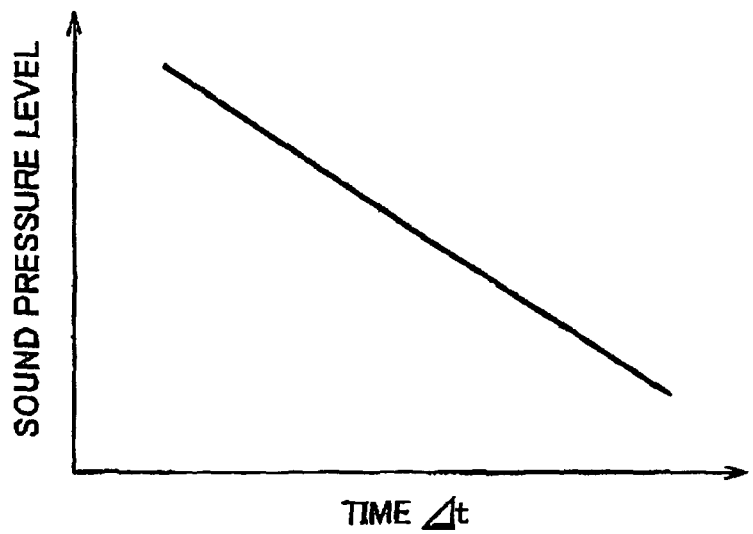
FIG. 8A shows the relationship between suitable values of the sound pressure level and the time Δt when a maintaining stimulus is to be applied.
Figure 8B:
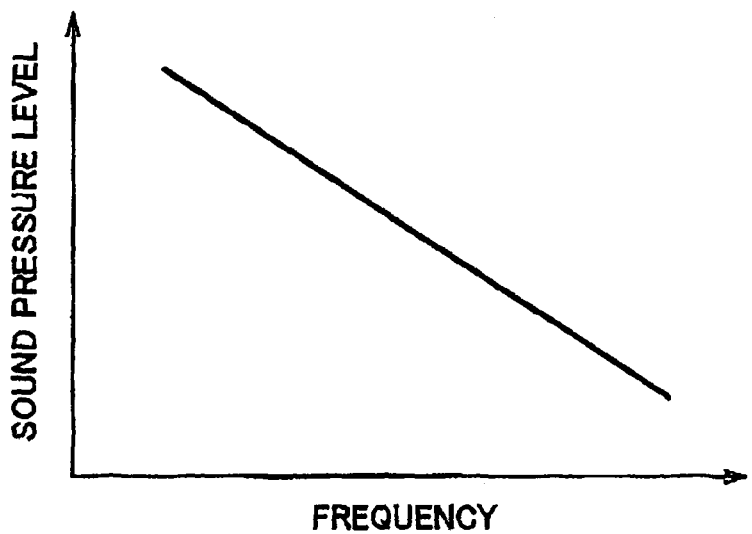
FIG. 8B shows the relationship between suitable values of the sound pressure level and the frequency when a maintaining stimulus is to be applied.

In the case where the comparison result of step S15 indicates that the current sleep depth level SL is the same as the target sleep depth level SL1, that is, the driver is sleeping at the target depth, the applied stimulus control section 16 actuates the stimulus application device 5 to apply to the driver a maintaining stimulus which maintains the sleep depth level of the driver (S18). The maintaining stimulus may be suitably selected from continuous application of feeble light or feeble vibration, an auditory stimulus such as repeatedly reproducing sound at a predetermined sound pressure level (about 55 dB of pink noise, for example) for time $\Delta t$ at a frequency of 30 seconds as shown in FIG. 7, etc. The predetermined sound pressure level is preferably lowered as the time $\Delta t$ increases as shown in FIG. 8A, and preferably lowered as the sound frequency increases as shown in FIG. 8B. More preferably, a sensory threshold stimulus to be used in a second embodiment to be discussed later is applied to the individual person.

After a stimulus is applied in one of steps S16 to S18, the process proceeds to step S19, where the current sleep time nt is compared with the sleep duration time T. In the case where the comparison result indicates that the current sleep time nt is less than the sleep duration time T, the process returns to step S11 to repeat maintenance control of the sleep depth level of the driver. In the case where the comparison result of step S19 indicates that the current sleep time nt is the sleep duration time T or more, an awakening stimulus that is several times more intense than the awakening stimulus applied to the driver in step S16 is applied to the driver to awaken the driver (S20). The first sleep control is thus terminated.

Now, a detailed description will be made of the second sleep control with reference to FIG. 6. The sequence of control processes of the second sleep control described below is executed by the control unit 2 repeatedly.

When the second sleep control is started, first, the physiological information detection section 3 executes physiological measurement again (S30). Then, the sleep depth level determination section 10 determines the current sleep depth level SL of the driver based on the physiological information from the physiological information detection section 3 such as the heart rate (S31). Subsequently, it is determined whether or not the current sleep depth level SL determined in step S31 is 4 which is the maximum level (S32).

In the case where the determination result of step S32 indicates that the current sleep depth level SL has not reached 4, a sleep-inducing stimulus is applied to the driver as necessary to increase the sleep depth level of the driver (S33). The sleep-inducing stimulus used in step S33 may be the same as the sleep-inducing stimulus used in S17 of the first sleep control.

In the case where the determination result of step S32 indicates that the current sleep depth level SL reaches 4, on the other hand, the process proceeds to step S34, where physiological measurement on the driver is executed again. Then, the sleep depth level determination section 10 determines the current sleep depth level SL of the driver in the same way as step S31, in order to determine whether or not the current sleep depth level SL is 2, which is lower than the sleep depth level 4 which is the maximum sleep depth level (step S36).

In the case where the determination result of step S36 indicates that the current sleep depth level SL has not reached 2, an awakening stimulus is applied to the driver as necessary to decrease the sleep depth level of the driver (S37). The awakening stimulus used in this step may be the same as the awakening stimulus used in S16 of the first sleep control.

In contrast, in the case where the determination result of step S36 indicates that the current sleep depth level SL is 2, an awakening stimulus that is several times more intense than the awakening stimulus applied to the driver in step S37 is applied to the driver to awaken the driver (S38). The second sleep control is thus terminated.

As described above, the sleep control device 1 in accordance with the first embodiment executes both the first sleep control corresponding to mild drowsiness (drowsiness levels 3 to 5) and the second sleep control corresponding to severe drowsiness (drowsiness level 6). In the first sleep control, one of the sleep patterns P1 to P3 is selected and set to provide a sleep pattern that maintains the sleep depth level of the driver at the sleep depth level 2, which is lower than the sleep depth level 4 which is the maximum level, for 5 to 30 minutes. In the second sleep control, in contrast, the sleep pattern 4 which utilizes the natural sleep rhythm of the driver is set to provide a sleep pattern that maintains the sleep depth level of the driver at the sleep depth level 4 for a while.

In this way, the sleep control device 1 relieves the drowsiness of the driver effectively by providing a sleep pattern that maintains the sleep depth level 2 when the driver is in mild drowsiness, and providing a sleep pattern that promotes fatigue recovery using natural sleep rhythms when the driver is in severe drowsiness. Thus, the sleep control device 1 can assist appropriate sleep according to the drowsiness of the driver.

In the first sleep control executed by the sleep control device 1 in accordance with the first embodiment, the duration times T1 to T3 are set such that the sleep depth level 2 is maintained for a longer time as the drowsiness level increases from 3 to 5. This allows providing further effective sleep assistance according to the degree of the drowsiness level.

In the first sleep control executed by the sleep control device 1 in accordance with the first embodiment, in addition, the current sleep depth level is compared with the target sleep depth level so that one of an awakening stimulus, a maintaining stimulus, and a sleep-inducing stimulus is applied to the driver according to the obtained difference between the levels. This ensures that the current sleep depth level of the driver is maintained at the sleep depth level 2 during one of the duration times T1 to T3.

In the second sleep control executed by the sleep control device 1 in accordance with the first embodiment, the current sleep depth level is compared with the target sleep depth level so that a sleep-inducing stimulus is applied to the driver in order to increase the current sleep depth level of the driver to the sleep depth level 4. This allows the current sleep depth level of the driver to immediately reach the sleep depth level 4.

In the second sleep control executed by the sleep control device 1 in accordance with the first embodiment, in addition, an awakening stimulus is applied to the driver to awaken him or her when the sleep depth level of the driver once reaches the sleep depth level 4 and then the sleep depth level 2. By awakening the driver from sleep at the sleep depth level 2, it is possible to suppress deterioration in the responsiveness of the driver compared to the case where the driver is awakened using natural sleep rhythms.

Now, a detailed description will be made of a second embodiment of the sleep control device in accordance with the invention with reference to the drawings. The same components as those of the first embodiment discussed above are denoted by the same reference numerals.

FIG. 9 shows the configuration of a sleep control device in accordance with a second embodiment of the invention. A sleep control device 9 shown in FIG. 1 is installed in vehicles such as automobiles. The sleep control device 1 assists a driver (individual person) of a vehicle to have appropriate sleep that matches the drowsiness level of the driver after parking the vehicle at a predetermined location when the driver is feeling drowsy while driving. The sleep control device 1 includes a sleep control section 2 which is an electronic control unit 2 that executes overall control of the sleep control device 1.

An operation input section 17 is connected to the sleep control section 2. The operation input section 17 allows selection and input of a sleep pattern. The operation input section 17 allows the driver to select and input a sleep pattern with a sleep depth level and a sleep time desired by the driver. The operation input section 17 may be a touch panel screen of a navigation system, for example, and may be installed in the control panel of the vehicle to allow the driver to select one of predetermined sleep patterns displayed on the touch panel screen. The operation input section 17 outputs information about the selected sleep pattern to the sleep control section 2.

A physiological information detection section 3 is also connected to the sleep control section 2. The physiological information detection section 3 detects physiological information of the driver. The physiological information detection section 3 detects physiological information such as the heart rate of the driver. The physiological information detection section 3 may be a heart rate measurement sensor that measures the heart rate, for example. The heart rate measurement sensor may be built in the back rest of a driver's seat to measure the heart rate of the driver, for example. When a sleep pattern is selected and input using the operation input section 17 to start the predetermined sleep pattern, the physiological information detection section 3 starts detecting physiological information. The physiological information detection section 3 outputs the detected physiological information to the sleep control section 2.

A sensory threshold detection section 18 is also connected to the sleep control section 2. The sensory threshold detection section 18 detects a sensory threshold of the driver being awakened. The sensory threshold detection section 18 may be constituted by an output part that applies an auditory stimulus such as sound, an amplifier capable of varying the sound pressure level (intensity) of the sound, and a switch operated by the driver when the sound is audible. The sensory threshold detection section 18 causes the output part to output sound at various sound pressure levels, allows the driver to operate the switch when he or she hears audible sound, and detects the minimum audible sound pressure level as the sensory threshold of the driver. The sensory threshold detection section 18 outputs information about the detected sensory threshold to the sleep control section 2. The output part may be headphones attached to the head rest of the driver's seat, for example. In this case, the sensory threshold can be detected without interference by stimuli from the surrounding environment.

An environmental stimulus intensity detection section 19 is also connected to the sleep control section 2. The environmental stimulus intensity detection section 19 detects the intensity of stimuli applied to the driver being asleep from the surrounding environment. The environmental stimulus intensity detection section 19 may be an omnidirectional microphone which may be installed in the head rest of the driver's seat, for example. The omnidirectional microphone may detect the intensity of stimuli applied to the driver from the surrounding environment such as noise, that is, the sound pressure level of the noise. The environmental stimulus intensity detection section 19 outputs information about the detected sound pressure level of the noise from the surrounding environment to the sleep control section 2.

A stimulus application device 5 is also connected to the sleep control section 2. The stimulus application device 5 applies a physical stimulus to the driver. The stimulus application device 5 may be a speaker that applies an auditory stimulus by reproducing sound, for example. The speaker may be built in the head rest of the driver's seat, for example.

The sleep control section 2 includes a sleep pattern storage section 12 that stores a plurality of sleep patterns, a sleep pattern selection setting section 20 that sets a target sleep pattern selected from the plurality of sleep patterns, a sleep time measurement section 14 that measures the elapsed time of the target sleep pattern, a sleep depth level determination section 10 that determines the current sleep depth level of the driver being asleep, a sleep depth level comparison section 15 that compares the current sleep depth level with the target sleep depth level in accordance with the target sleep pattern, and an applied stimulus control section 16 that sets a sensory threshold stimulus having an intensity defined based on the sensory threshold of the driver in the case where the current sleep depth level reaches the target sleep depth level.

The "sleep depth level" used in the second embodiment is an index representing the depth of sleep, and classified into four levels from level 1 which corresponds to light sleep to level 4 which corresponds to deep sleep, as shown in FIG. 2 referenced in relation to the first embodiment. Specifically, the sleep depth level 1 corresponds to light sleep such as dozing, the sleep depth level 2 corresponds to such light sleep that sleep breaths may be heard, the sleep depth level 3 corresponds to deep sleep in which sensation has been almost lost, and the sleep depth level 4 corresponds to sleep at the maximum depth level.

The sleep pattern storage section 12 stores at least three sleep patterns with respective sleep depth levels and sleep times. The at least three sleep patterns include the sleep patterns P1 to P3 shown in FIG. 2 referenced in relation to the first embodiment. The three sleep patterns have a common target sleep depth level 2, which is lower than the maximum sleep depth level, and different target sleep times of 5 minutes, 10 minutes, and 30 minutes. In order to allow the driver to also select the sleep pattern P4 which utilizes natural sleep rhythms as in the first embodiment, the sleep pattern storage section 12 may store four sleep patterns including the sleep pattern P4.

The sleep pattern selection setting section 20 selects one of the three sleep patterns P1 to P3 stored in the sleep pattern storage section 12 that is chosen by the driver by operating the operation input section 17, to set the selected sleep pattern as the target sleep pattern. Information about the target sleep pattern set by the sleep pattern selection setting section 20 is output to the sleep time measurement section 14 and the sleep depth level comparison section 15.

The sleep time measurement section 14 measures a sleep time, which is the elapsed time from the start of the target sleep pattern selected and set by the sleep pattern selection setting section 20. The sleep time measurement section 14 outputs the measured sleep time to the sleep pattern selection setting section 20 and the sleep depth level comparison section 15.

The sleep depth level determination section 10 determines the current sleep depth level of the driver. After a sleep pattern control start signal is received from the sleep pattern selection setting section 20, the sleep depth level determination section 10 determines the current sleep depth level of the driver based on the heart rate detected by the physiological information detection section 3. The sleep depth level determination section 10 outputs the determined current sleep depth level to the sleep depth level comparison section 15.

The sleep depth level comparison section 15 compares the current sleep depth level determined by the sleep depth level determination section 10 with the target sleep depth level in accordance with the target sleep pattern selected by the sleep pattern selection setting section 20. The sleep depth level comparison section 15 compares the current sleep depth level with the target sleep depth level to output to the applied stimulus control section 16 a comparison signal indicating whether or not the current sleep depth level reaches the target sleep depth level.

The applied stimulus control section 16 includes a sensory threshold setting section 21 that sets a sensory threshold, a sensory threshold stimulus pattern storage section 23 that stores a plurality of sensory threshold stimulus patterns, and a sensory threshold stimulus setting section 22 that selects, and sets, one of the sensory threshold stimulus patterns. The sensory threshold setting section 21 sets the sensory threshold of the driver. The sensory threshold setting section 21 sets the sound pressure level detected by the sensory threshold detection section 18 as the sensory threshold of the driver, to output to the sensory threshold stimulus setting section 22 the sound pressure level defined based on the sensory threshold.

The sensory threshold stimulus pattern storage section 23 stores eight sensory threshold stimulus patterns that emit sound at a predetermined sound pressure level intermittently at a certain frequency. The eight sensory threshold stimulus patterns are all a stimulus pattern with a frequency of one minute in which sound at a predetermined sound pressure level is emitted intermittently at intervals of 15 seconds, as shown in FIG. 10. The sound pressure levels of the sensory threshold stimulus patterns are 30 dB, 40 dB, 50 dB, 60 dB, 70 dB, 80 dB, 90 dB, and 100 dB, respectively.

Figure 11:
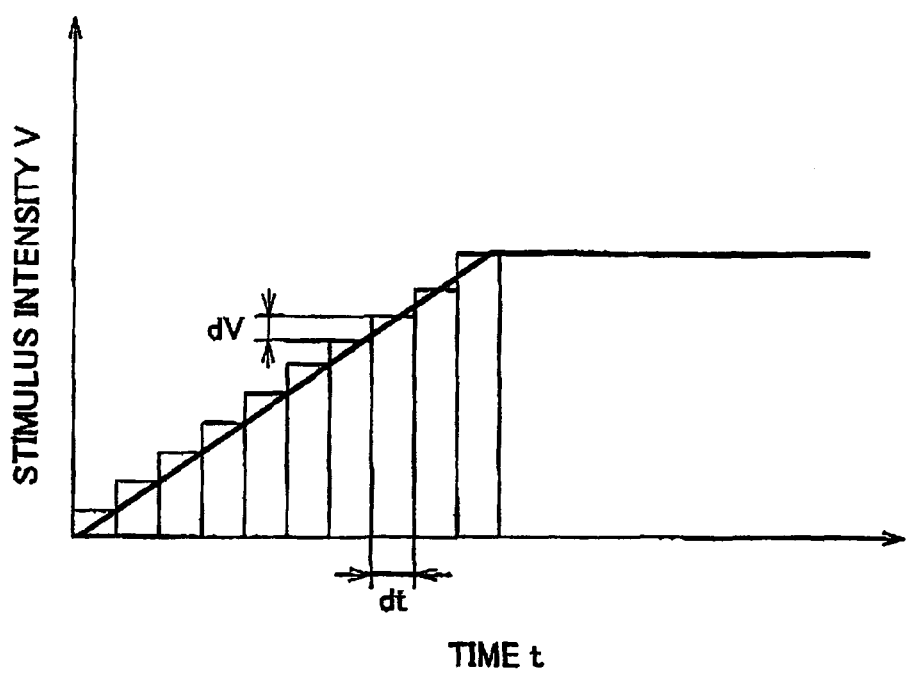
FIG. 11 schematically shows changes in the intensity of a sensory threshold stimulus made based on a discrimination threshold.

In the sensory threshold stimulus patterns, when the application of a stimulus is started, the intensity of the stimulus is gradually increased to reach the predetermined sound pressure level, as shown in FIG. 10. This is because the driver may perceive a change in the stimulus intensity in the case where the change is so rapid, and in order to prevent such a change, the sound pressure level is changed based on a change rate of a human discrimination threshold or less. That is, when the application of a stimulus is started, the sound pressure level is changed such that when defining a human intensity discrimination threshold for the sensory threshold stimulus as dV and a human time discrimination threshold for the sensory threshold stimulus as dt, the change in the intensity of the sensory threshold stimulus per unit time is dV/dt or less, as shown in FIG. 11. When the application of a stimulus is terminated, the intensity of the stimulus is gradually decreased in the same way.

An exemplary manner of stimulus application is shown in FIG. 12. In the case of applying a sensory threshold stimulus pattern at a sound pressure level of 40 dB, for example, the sound pressure level is gradually increased from 0 dB to 40 dB in 3 seconds at the start of the application, then maintained at 40 dB for 9 seconds, and then gradually decreased from 40 dB to 0 dB in 3 seconds at the termination of the application. The process of stimulus application is performed intermittently at a predetermined frequency.

The sensory threshold stimulus setting section 22 selects, and sets, one of the eight sensory threshold stimulus patterns discussed above stored in the sensory threshold stimulus pattern storage section 23 that has the predetermined intensity. The sensory threshold stimulus setting section 22 selects, and sets, one of the eight sensor threshold stimulus patterns corresponding to the sensory threshold stimulus having an intensity defined based on the sensory threshold of the driver detected by the sensory threshold detection section 18 and set by the sensory threshold setting section 21.

In the case where stimuli such as noise are applied to the driver being asleep from the surrounding environment, the sensory threshold stimulus setting section 22 selects, and sets, one of the sensory threshold stimulus patterns that has a predetermined intensity not only based on the sensory threshold but also based on the stimuli such as noise from the surrounding environment detected by the environmental stimulus intensity detection section 19. In this case, the sensory threshold stimulus setting section 22 selects, and sets, one of the eight sensory threshold stimulus patterns corresponding to the sensory threshold stimulus having an intensity defined based on the sound pressure level obtained by subtracting the sound pressure level of the noise detected by the environmental stimulus intensity detection section 19 from the sound pressure level detected by the sensory threshold detection section 18.

When a comparison signal indicating that the current sleep depth level reaches the target sleep depth level is received from the sleep depth level comparison section 15, the sensory threshold stimulus setting section 22 outputs a stimulus application signal to the stimulus application device 5 to cause the stimulus application device 5 to apply to the driver a predetermined sensory threshold stimulus pattern having an intensity defined based on the sensory threshold discussed above. When the stimulus application signal is received from the sensory threshold stimulus setting section 22, the stimulus application device 5 applies to the driver a stimulus at a predetermined sound pressure level intermittently for one minute according to the sensory threshold stimulus pattern. The sensory threshold stimulus setting section 22 repeatedly sets, and changes as necessary, the sensory threshold stimulus pattern, to continue outputting a predetermined stimulus application signal to the stimulus application device 5 until the sleep time in accordance with the target sleep pattern elapses.

Figure 13:
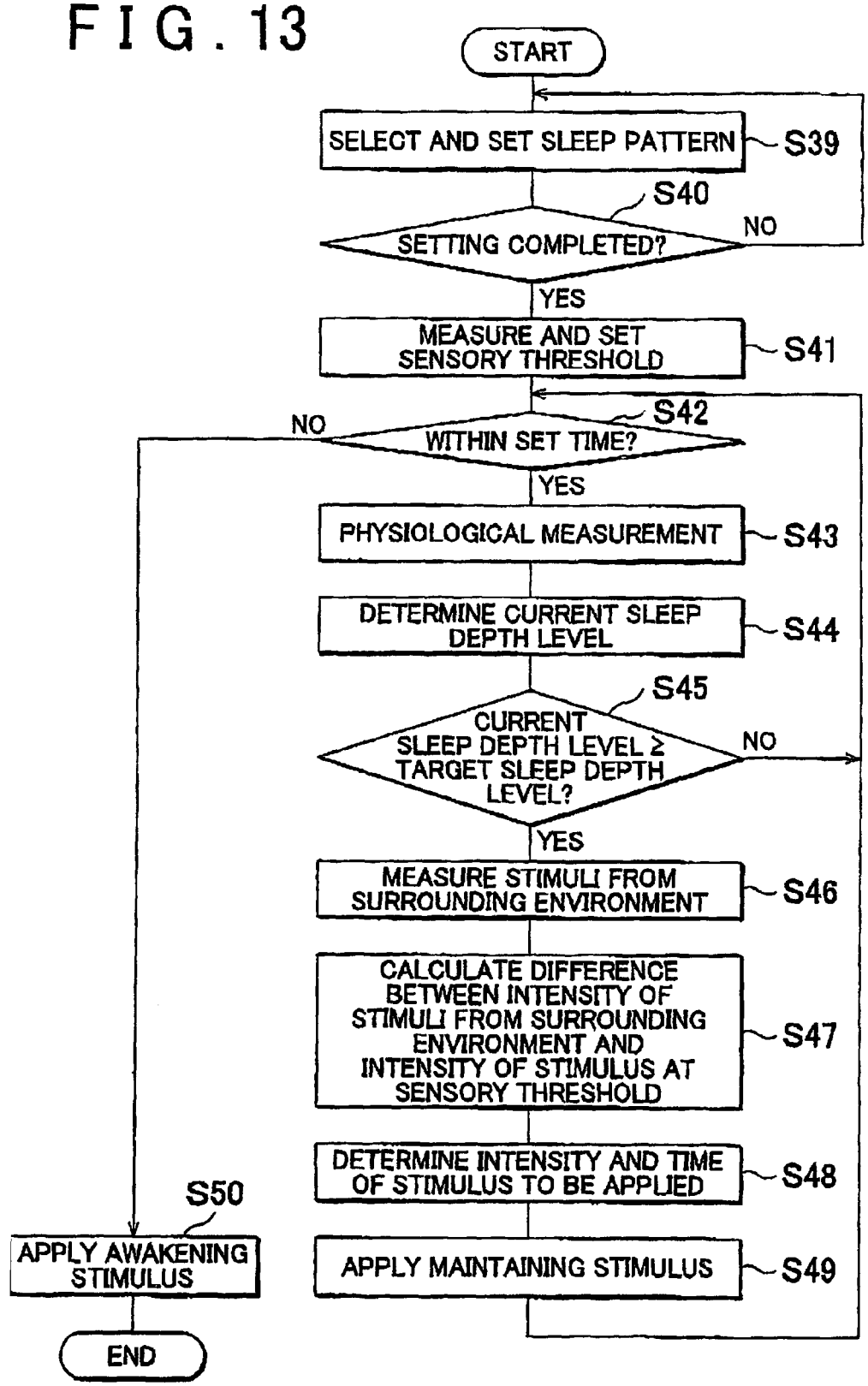
FIG. 13 is a flowchart showing the operation of the sleep control device in accordance with the second embodiment shown in FIG. 9.

Now, a description will be made of the operation of the aforementioned sleep control device 1 with reference to the flowchart shown in FIG. 13. The sequence of control processes described below is executed by the sleep control section 2 repeatedly for a predetermined time.

First, in step S39, one of the at least three sleep patterns P1 to P3 (with the target sleep depth level being 2 and the target sleep time being 5 minutes, 10 minutes, and 30 minutes, respectively) stored in the sleep pattern storage section 12 is selected using the operation input section 17, and a signal indicating the selected sleep pattern is output to the sleep pattern selection setting section 20, which sets the selected sleep pattern. Step S39 is repeated until the setting of the sleep pattern is completed. When the setting of the sleep pattern is completed (S40), the process proceeds to step S41.

Then, the sensory threshold of the awakened driver is measured (S41). In the measurement, the driver puts on the headphones of the sensory threshold detection section 18, by which sound is reproduced at various sound pressure levels. The sensory threshold of the driver is measured by detecting the sound pressure level as the sensory threshold. The measured sensory threshold is set by the sensory threshold setting section 21.

When the sensory threshold is set in step S41, the sleep pattern is started. First, it is determined whether or not the elapsed time measured by the sleep time measurement section 14 is within the time set in accordance with the sleep pattern (S42). In the case where the elapsed time is within the set time, the process proceeds to step S43, where a physiological measurement process is executed. In the physiological measurement process, the heart rate sensor of the physiological information detection section 3 detects the heart rate of the driver to measure the physiological state of the driver.

When the heart rate of the driver is detected in step S43, the sleep depth level determination section 10 determines the current sleep depth level of the driver based on the physiological information such as the heart rate (S44). Thereafter, the sleep depth level comparison section 15 compares the current sleep depth level determined in step S44 with the target sleep depth level in accordance with the target sleep pattern selected and set in step S39 (S45).

In the case where the comparison result of step S45 indicates that the current sleep depth level is lower than the target sleep depth level, the process proceeds to step S42 to repeat the elapsed time determination in step S42, the physiological measurement in step S43, and the current sleep depth level determination in step S44. In contrast, in the case where the current sleep depth level is equal to the target sleep depth level or higher, that is, it is determined that the current sleep depth level reaches the target sleep depth level, the process proceeds to step S46, where the intensity of stimuli applied to the driver from the surrounding environment is measured.

In step S46, the environmental stimulus intensity detection section 19 measures the intensity of stimuli from the surrounding environment by detecting the sound pressure level of noise as the intensity of stimuli applied to the driver being asleep from the surrounding environment. When the sound pressure level of the noise from the surrounding environment is detected, a differential is calculated by subtracting the sound pressure level of the noise from the surrounding environment from the sound pressure level as the sensory threshold set in step S41 (S47). In the case where the sound pressure level of the noise from the surrounding environment measured in step S46 is extremely low, the detected sound pressure level is set to 0 dB before executing the following processes.

Subsequently, one of the eight sensory threshold stimulus patterns (with the frequency being one minute and the sound pressure level being 30 dB, 40 dB, 50 dB, 60 dB, 70 dB, 80 dB, 90 dB, and 100 dB, respectively) which is stored in the sensory threshold stimulus pattern storage section 23, and whose sound pressure level is the most approximate to the differential calculated in step S47, is selected to determine the sound pressure level and the frequency, or the time, with which sound is to be applied to the driver as the sensory threshold stimulus (S48). When the sound pressure level and the time of sound as the sensory threshold stimulus are determined, the sensory threshold stimulus setting section 22 outputs a stimulus application signal to the stimulus application device 5 based on the determined sound pressure level and time. The stimulus application device 5 applies a predetermined sensory threshold stimulus to the driver based on the stimulus application signal (S49). When the sensory threshold stimulus is applied for one minute corresponding to the predetermined frequency in step S49, the process returns to step S42 to repeat the predetermined processes.

Thereafter, in the case where it is determined in step S42 that the time set in accordance with the target sleep pattern has been elapsed, the process proceeds to step S50, where the stimulus application device 5 applies an awakening stimulus which is more intense than the sensory threshold to awaken the driver. The sleep control is thus terminated.

As described above, the sleep control device 1 in accordance with the second embodiment applies to the driver sound having a sound pressure level defined based on the sensory threshold for 5 minutes, 10 minutes, or 30 minutes in the case where the current sleep depth level of the driver reaches the target sleep depth level. By applying the sensory threshold stimulus in this way, the sleep depth level of the driver can be maintained at a low level which may be the sleep depth level 2. This allows the driver to feel significantly refreshed when he or she wakes up even after short sleep of 5 minutes to 30 minutes.

The sleep control device 1 in accordance with the second embodiment applies to the driver, as the sensory threshold stimulus, sound at the sound pressure level obtained by subtracting the sound pressure level of the noise detected by the environmental stimulus intensity detection section 19 from the sound pressure level determined based on the sensory threshold detected by the sensory threshold detection section 18. By applying the sensory threshold stimulus at the sound pressure level defined based on the sensory threshold minus the sound pressure level of the noise that the driver receives from the surrounding environment, the sleep depth level of the driver can further reliably be maintained at a low level which may be the sleep depth level 2.

The sleep control device 1 in accordance with the second embodiment applies the sensory threshold stimulus pattern as an intermittent stimulus. If the applied sound pressure level is constant, the driver being asleep may adapt to that sound pressure level, and thus the responsiveness of the driver to the particular sound pressure level may deteriorate. By intermittently applying to the driver sound at the sound pressure level as the sensory threshold stimulus, the sleep depth level of the driver can further reliably be maintained at a low level which may be the sleep depth level 2.

When applying the sensory threshold stimulus, the sleep control device 1 in accordance with the second embodiment gradually increases and decreases the sound pressure level, or the intensity, of the sensory threshold stimulus applied intermittently, such that the sound pressure level changes at a rate lower than the human discrimination threshold. A rapid change in the stimulus intensity may awaken the driver during sleep. Thus, by changing the intensity of the sensory threshold stimulus at a rate lower than the human discrimination threshold, the sleep depth level of the driver can be maintained at a predetermined level further reliably without awakening the driver during sleep. Since the driver is less frequently awakened during sleep, the driver can feel further refreshed.

In the sleep control device 1 in accordance with the second embodiment, the sleep depth level determination section 10 determines the current sleep depth level of the driver based on the heart rate detected by the heart rate measurement sensor as the physiological information detection section 3. This allows the current sleep depth level of the driver to be determined precisely based on the physiological information such as the heart rate of the individual person.

Subsequently, a description will be made of a sleep depth level maintenance test performed on a subject using the aforementioned sleep control device.

Figure 14:
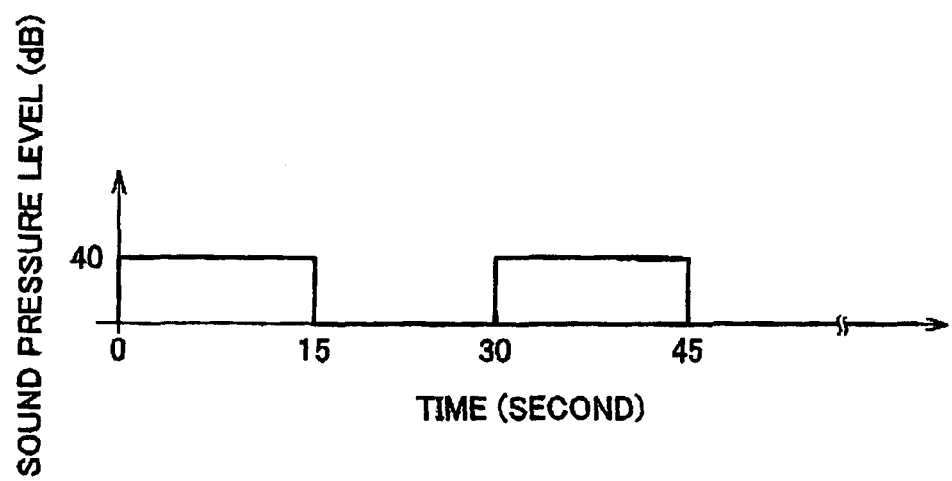
FIG. 14 shows a sensory threshold stimulus pattern for use in a sleep depth level maintenance test.

[Sleep Depth Level Maintenance Test] The test was conducted to compare how the sleep depth level of a subject changed after he or she started sleeping between the case where the sensory threshold stimulus was applied or not to the subject. As the sensory threshold stimulus applied to the subject in the maintenance test, a sensory threshold stimulus at a sound pressure level of 40 dB was applied at intervals of 15 seconds, as shown in FIG. 14.

Figure 15:
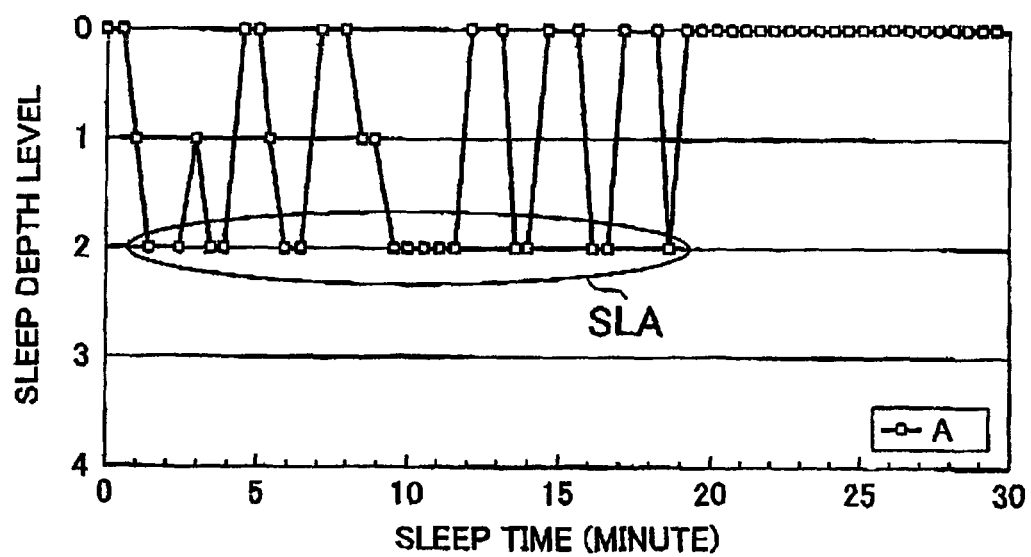
FIG. 15 shows the results of a sleep depth level maintenance test in which a sensory threshold stimulus was applied.
Figure 16:
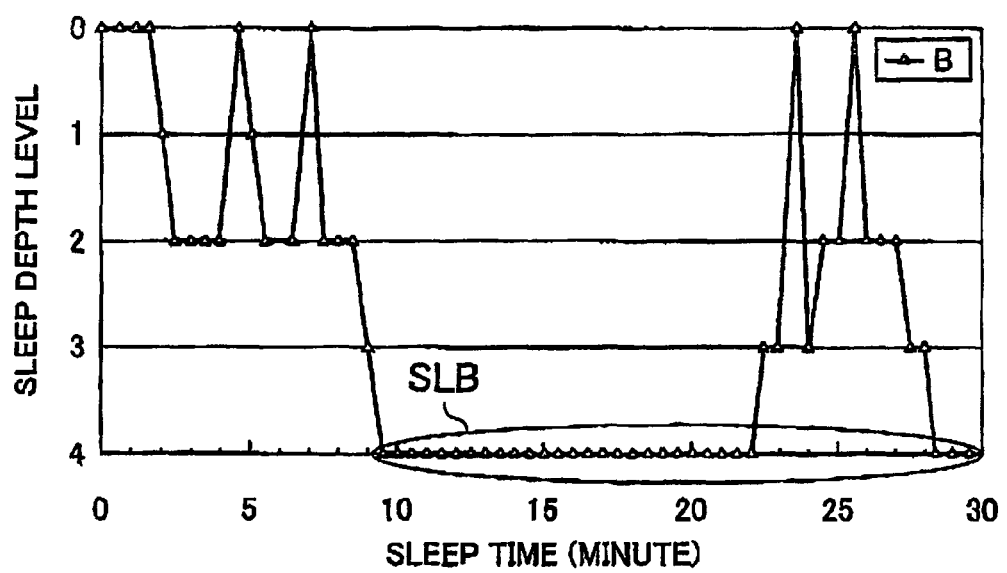
FIG. 16 shows the results of a sleep depth level maintenance test in which a sensory threshold stimulus was not applied.

FIG. 15 shows the test results (A) obtained in the case where the sensory threshold stimulus was applied to the subject being asleep. As shown in the drawing, in the case where the sensory threshold stimulus as shown in FIG. 14 was applied to one subject, the sleep depth level of the subject was maintained at the sleep depth level 2 for about 15 to 20 minutes, as indicated by SLA. Meanwhile, FIG. 16 shows the test results (B) obtained in the case where the sensory threshold stimulus was not applied to the subject being asleep. As shown in the drawing, in the case where the sensory threshold stimulus was not applied to one subject, the sleep depth level of the subject was increased gradually with some fluctuations based on wakefulness rhythms, as natural sleep rhythms, to finally reach the sleep depth level 4 which was the deepest level.

The test results confirmed that the sleep depth level of the subject can be maintained at the sleep depth level 2 which is lower than the maximum level for a certain time by applying to the subject the sensory threshold stimulus having an intensity defined based on the human sensory threshold.

Now, a description will be made of a number-of-awakenings test performed on a subject using the aforementioned sleep control device.

[Number-of-Awakenings Test] The test was conducted to compare how many times a subject was awakened since he or she started sleeping in the case where the sensory threshold stimulus was applied at a change rate of the human discrimination threshold or less with how many times the subject was awakened in the case where the sensory threshold stimulus was applied at a change rate more than the human discrimination threshold. As the sensory threshold stimulus applied at a change rate of the human discrimination threshold or less in the number of awakenings test, a sensory threshold stimulus at a sound pressure level of 40 dB was applied at intervals of 15 seconds with the sound pressure level increased from 0 dB to 40 dB and decreased from 40 dB to 0 dB in 3 seconds at the start and termination of the application, respectively, as shown in FIG. 17. Meanwhile, as the sensory threshold stimulus applied at a change rate more than the human discrimination threshold, a sensory threshold stimulus at a sound pressure level of 40 dB with a rectangular waveform was applied at intervals of 15 seconds, as shown in FIG. 14.

Figure 18:
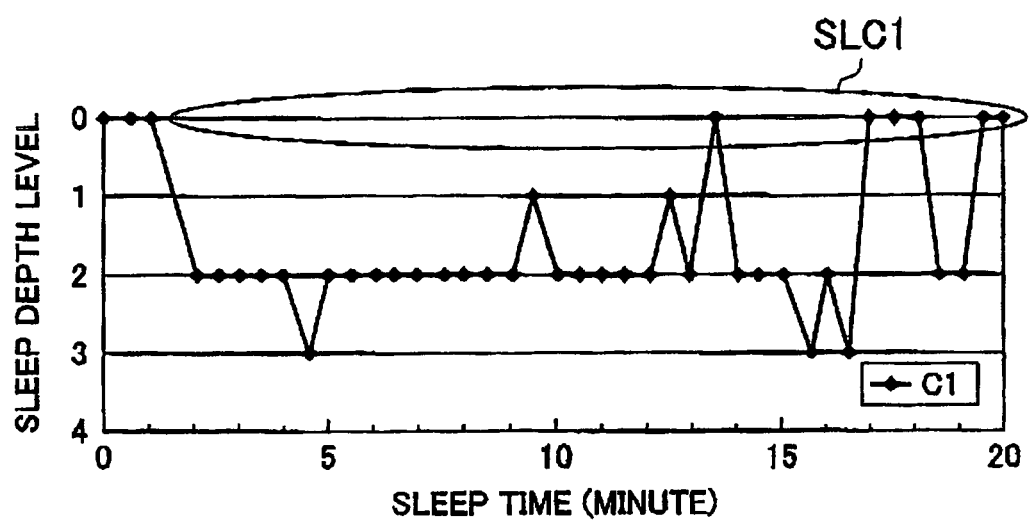
FIG. 18 shows the results of a number-of-awakenings test in which a sensory threshold stimulus was applied at a change rate of the discrimination threshold or less.
Figure 19:
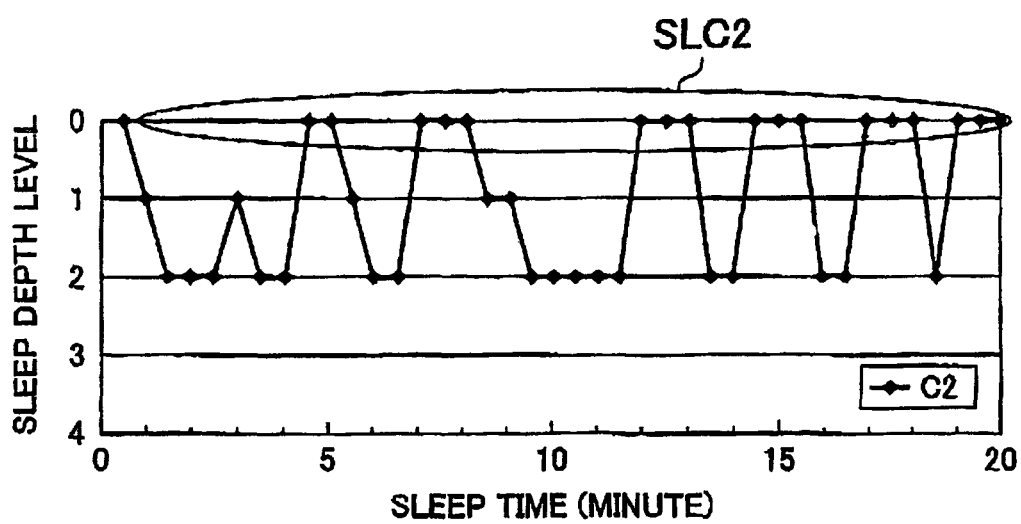
FIG. 19 shows the results of a number-of-awakenings test in which a sensory threshold stimulus was applied at a change rate more than the discrimination threshold.

FIG. 18 shows the test results (C1) obtained in the case where the sensory threshold stimulus was applied at a change rate of the human discrimination threshold or less. As shown in the drawing, the sleep depth level of one subject was maintained at the sleep depth level 2 for 20 minutes, during which the subject was awakened only three times, as indicated by SLC1. Meanwhile, FIG. 19 shows the test results (C2) obtained in the case where the sensory threshold stimulus was applied at a change rate more than the human discrimination threshold. As shown in the drawing, the sleep depth level of one subject was maintained at the sleep depth level 2 for 20 minutes, during which the subject was awakened six times, as indicated by SLC2.

The test results confirmed that the sleep depth level of the subject can be maintained at the sleep depth level 2 and, further, the number of awakenings of the subject during sleep can be reduced by applying to the subject the sensory threshold stimulus at a change rate of the human discrimination threshold or less.

The aforementioned second embodiment merely gives an example of the sleep control device in accordance with the invention. The sleep control device in accordance with the invention, however, is not limited thereto. For example, although the sound pressure level is used as the intensity of the stimulus in the second embodiment, the sound frequency may be used as the intensity of the stimulus in place of or in addition to the sound pressure level. Although the current sleep depth level is measured based on the measurement of a physiological factor such as the heart rate in the second embodiment, the current sleep depth level may be measured based on the measurement of other physiological factors such as brain waves.

Figure 20A:
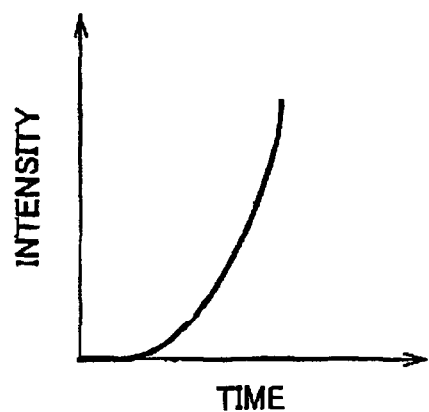
FIG. 20A shows another example in which the intensity of a sensory threshold stimulus is changed exponentially based on the discrimination threshold.
Figure 20B:
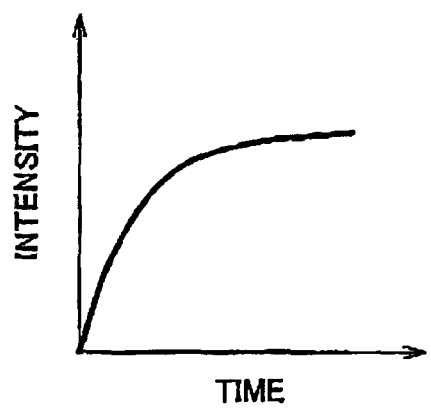
FIG. 20B shows still another example in which the intensity of a sensory threshold stimulus is changed logarithmically based on the discrimination threshold.
Figure 20C:
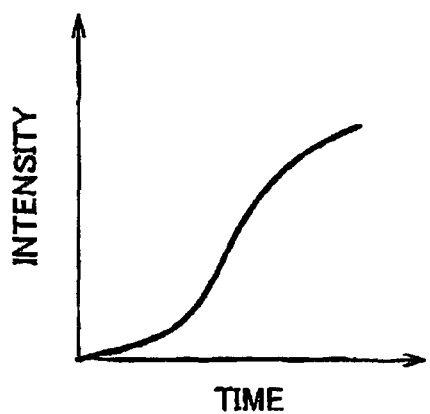
FIG. 20C shows yet another example in which the intensity of a sensory threshold stimulus is changed sinusoidally based on the discrimination threshold.

In the case where the intensity of the sensory threshold stimulus is changed based on the human discrimination threshold in the second embodiment, the intensity is changed along a line represented by a linear function, as shown in FIG. 11. However, the intensity may be changed along a curve represented by an exponential function, as shown in FIG. 20A, as long as the change is based on the human discrimination threshold. Alternatively, the intensity may be changed along a curve represented by a logarithmic function, as shown in FIG. 20B. Still alternatively, the intensity may be changed along a curve represented by a sinusoidal function, as shown in FIG. 20C.

The first embodiment and the second embodiment may be implemented separately, or may be implemented in combination. For example, in the case where the sleep control device in accordance with the second embodiment is applied to the first embodiment, when the driver is taking a nap using one of the sleep patterns P1 to P3 and the stimulus application device 5 is to apply an awakening stimulus to decrease the sleep depth level of the driver, the awakening stimulus may be applied using the sensory threshold stimulus pattern set by the sensory threshold stimulus setting section 22 of the second embodiment.

The aforementioned first embodiment and second embodiment merely give an example of the sleep control device in accordance with the invention. However, the sleep control device in accordance with the invention is not limited thereto, and the sleep control device in accordance with the first embodiment and the second embodiment may be modified or applied to objects other than vehicles without departing from the scope and spirit of the invention. For example, although the drowsiness level and the current sleep depth level are measured based on the measurement of physiological factors such as the number of blinks and the heart rate in the embodiments, the drowsiness level and the current sleep depth level may be measured based on the measurement of other physiological factors such as brain waves and the breathing rate.

Although the drowsiness level is measured based on the physiological measurement in the first and second embodiments, the drowsiness level may be measured based on psychological measurement such as by questioning and behavioral measurement such as the vehicle state or the driver's behavior (such as the driving time and the zigzag amount of the vehicle). The drowsiness level may be measured in consideration of the fatigue level of the driver by making the driver to input the time at which he or she slept last night, the time at which he or she woke up in the morning that day, etc.

Although the term "drowsiness level" is used to refer to the degree of drowsiness in the first embodiment and the second embodiment, the degree of drowsiness may also be referred to as "wakefulness level". Although the term "sleep depth level" is used to refer to the depth level of sleep in the embodiments, the depth level of sleep may also be referred to as "sleep stage" which is an international index.

Although the sleep control device in accordance with the invention is applied to a vehicle in the first embodiment and the second embodiment, the sleep control device in accordance with the invention may be applied to other than vehicles, such as beds and relaxing chairs, for refreshment purposes for those engaged in ordinary jobs and for napping purposes for those engaged in jobs that do not permit taking long hours of nap such as police officers and fire fighters.

The invention claimed is:

1. A sleep control device comprising:
an electronic control unit;
a sensor configured to detect a physiological information of the individual person and output to the electronic control unit,
wherein the electronic control unit is configured to receive the output of the sensor, detect a drowsiness level of the individual person, and output the detected drowsiness level to a sleep pattern selection section;
wherein the electronic control unit contains a plurality of predetermined sleep patterns matched to respective drowsiness levels, each of the predetermined sleep patterns having a target sleep depth level and a target sleep time, the target sleep depth levels of the plurality of predetermined sleep patterns matching drowsiness levels equal to or below a predetermined drowsiness level being a predetermined sleep depth level and the target sleep depth levels of the plurality of predetermined sleep patterns matching drowsiness levels exceeding the predetermined drowsiness level being a maximum sleep depth level;

wherein the electronic control unit is configured to select one of the plurality of predetermined sleep patterns that matches the detected drowsiness level contained in the electronic control unit;

wherein the electronic control unit is configured to control the sleep depth level of the individual person in accordance with the target sleep depth level and the target sleep time of the selected predetermined sleep pattern; and wherein the electronic control unit is configured to execute a first sleep control to maintain the sleep depth level of the individual person at the predetermined sleep depth level below the maximum sleep depth level for the target sleep time, if the detected drowsiness level is equal to or below the predetermined drowsiness level.

2. The sleep control device according to claim 1, wherein the electronic control unit further is configured to determine the sleep depth level of the individual person based on the physiological information detected by the sensor.

3. The sleep control device according to claim 2, further comprising:

a stimulus application device;

wherein the electronic control unit is configured to control the stimulus application device to apply a stimulus to the individual person based on the sleep depth level determined by the electronic control unit.

4. The sleep control device according to claim 3, wherein the electronic control unit controls the stimulus application device to apply an awakening stimulus to the individual person in order to decrease the sleep depth level if the sleep depth level determined by the electronic control unit is higher than the predetermined sleep depth level during the first sleep control.

5. The sleep control device according to claim 3, wherein the electronic control unit is configured to apply a sleep-inducing stimulus to the individual person in order to increase the sleep depth level if the sleep depth level determined by the electronic control unit is below the predetermined sleep depth level during the first sleep control.

6. The sleep control device according to claim 5, wherein the electronic control unit compares a current sleep depth level with the target sleep depth level, wherein the electronic control unit applies a sensory threshold stimulus, having an intensity defined based on a human sensory threshold, to the individual person if the electronic control unit determines that the current sleep depth level reaches the target sleep depth level.

7. The sleep control device according to claim 3, wherein the electronic control unit compares a current sleep depth level determined by the electronic control unit with the target sleep depth level, wherein the electronic control unit applies a sensory threshold stimulus, having an intensity defined based on a human sensory threshold, to the individual person if the electronic control unit determines that the current sleep depth level reaches the target sleep depth level.

8. The sleep control device according to claim 7, further comprising:

a sensory threshold detection section that detects a sensory threshold intensity defined by a sensory threshold of the individual person; and an environmental stimulus intensity detection section that detects an intensity of an environmental stimulus that the individual person receives from a surrounding environment, wherein the electronic control unit applies a stimulus to the individual person with an intensity obtained by subtracting the detected environmental stimulus intensity from the detected sensory threshold intensity as the sensory threshold stimulus.

9. The sleep control device according to claim 7, wherein the electronic control unit applies the sensory threshold stimulus to the individual person intermittently.

10. The sleep control device according to claim 7, wherein the electronic control unit applies the sensory threshold stimulus to the individual person so that a change in the intensity of the sensory threshold stimulus per unit time is $dV/dt$ or less, in which a human intensity discrimination threshold for the sensory threshold stimulus is defined as $dV$ and a human time discrimination threshold for the sensory threshold stimulus is defined as $dt$.

11. The sleep control device according to claim 2, wherein the electronic control unit detects the drowsiness level of the individual person based on the physiological information detected by the sensor.

12. The sleep control device according to claim 11, wherein the electronic control unit compares a current sleep depth level with the target sleep depth level, wherein the electronic control unit applies a sensory threshold stimulus, having an intensity defined based on a human sensory threshold, to the individual person if the electronic control unit determines that the current sleep depth level reaches the target sleep depth level.

13. The sleep control device according to claim 1, wherein the electronic control unit executes a second sleep control in which the sleep depth level of the individual person is maintained at a level that is higher than the predetermined sleep depth level at which the sleep depth level is maintained during the first sleep control, utilizing natural sleep rhythms of the individual person if the drowsiness level detected by the electronic control unit exceeds the predetermined drowsiness level.

14. The sleep control device according to claim 13, wherein the electronic control unit is configured to determine the sleep depth level of the individual person based on the physiological information detected by the sensor.

15. The sleep control device according to claim 14, further comprising:

a stimulus application device;

wherein the electronic control unit is configured to control the stimulus application device to apply a stimulus to the individual person based on the sleep depth level determined by the electronic control unit.

16. The sleep control device according to claim 15, wherein the electronic control unit controls the stimulus application device to apply a sleep-inducing stimulus to the individual person in order to increase the sleep depth level until the sleep depth level determined by the electronic control unit reaches the maximum sleep depth level during the second sleep control.

17. The sleep control device according to claim 15, wherein the electronic control unit controls the stimulus application device to apply an awakening stimulus to the individual person in order to awaken the individual person when the determined sleep depth level decreases to the predetermined sleep depth level after reaching the maximum sleep depth level.

18. The sleep control device according to claim 1, wherein the electronic control unit sets a time period over which the first sleep control is executed in accordance with the drowsiness level detected by the electronic control unit.

19. The sleep control device according to claim 18, further comprising:
a stimulus application device controlled by the electronic control unit;
wherein the electronic control unit controls the stimulus application device to apply an awakening stimulus to the individual person in order to awaken the individual person after the time period has elapsed during the first sleep control.

20. The sleep control device according to claim 18, wherein the electronic control unit detects the drowsiness level of the individual person based on the physiological information detected by the sensor.

21. The sleep control device according to claim 18,
wherein the electronic control unit compares a current sleep depth level with the target sleep depth level,
wherein the electronic control unit applies a sensory threshold stimulus, having an intensity defined based on a human sensory threshold, to the individual person if the electronic control unit determines that the current sleep depth level reaches the target sleep depth level.

22. A sleep control device comprising:
an electronic control unit;
a stimulus application device; and
a sensor configured to detect a physiological information of the individual person and output to the electronic control unit;
wherein the electronic control unit is configured to determine a current sleep depth level of the individual person;
wherein the electronic control unit contains a plurality of predetermined sleep patterns matched to respective drowsiness levels, each of the predetermined sleep patterns having a target sleep depth level;
wherein the electronic control unit is configured to select one of the plurality of predetermined sleep patterns that matches a detected drowsiness level;
wherein the electronic control unit is configured to compare the determined current sleep depth level with the target sleep depth level;
wherein the electronic control unit is configured to control the stimulus application device that applies a sensory threshold stimulus having an intensity defined based on a human sensory threshold to the individual person if the electronic control unit determines that the current sleep depth level reaches the target sleep depth level;
a sensory threshold detection section configured to detects a sensory threshold intensity defined by a sensory threshold of the individual person and output information to the electronic control unit; and
an environmental stimulus intensity detection section configured to detects an environmental stimulus intensity of a stimulus that the individual person receives from a surrounding environment and output information to the electronic control unit,
wherein the stimulus application device applies a stimulus to the individual person with an intensity obtained by subtracting the detected environmental stimulus intensity from the detected sensory threshold intensity, as the sensory threshold stimulus.

23. The sleep control device according to claim 22, wherein the electronic control unit applies the sensory threshold stimulus to the individual person intermittently.

24. The sleep control device according to claim 22, wherein the electronic control unit applies the sensory threshold stimulus to the individual person so that a change in the intensity of the sensory threshold stimulus per unit time is dV/dt or less, in which a human intensity discrimination threshold for the sensory threshold stimulus is defined as dV and a human time discrimination threshold for the sensory threshold stimulus is defined as dt.

25. The sleep control device according to claim 22,
wherein the electronic control unit detects the current sleep depth level of the individual person based on the physiological information detected by the sensor.

26. The sleep control device according to claim 22, wherein the sensory threshold stimulus has a minimum intensity that can be sensed by an awakened human.

27. A method of controlling a sleep control device, comprising:
providing a sleep control device having an electronic control unit,
wherein the electronic control unit contains a plurality of predetermined sleep patterns which match respective drowsiness levels, each of the predetermined sleep patterns having a target sleep depth level and a target sleep time of the target sleep depth level, the target sleep depth levels of the plurality of predetermined sleep patterns matching drowsiness levels equal to or below a predetermined drowsiness level being a predetermined sleep depth level and the target sleep depth levels of the plurality of predetermined sleep patterns matching drowsiness levels exceeding the predetermined drowsiness level being a maximum sleep depth level;
detecting a current drowsiness level of an individual person with the electronic control unit using physiological information from a sensor;
selecting one of the plurality of predetermined sleep patterns stored in the electronic control unit with the detected drowsiness level of the individual person, each of the predetermined sleep patterns having the target sleep depth level and the target sleep time of the target sleep depth level, the target sleep depth levels of the plurality of predetermined sleep patterns matching drowsiness levels equal to or below the predetermined drowsiness level being the predetermined sleep depth level and the target sleep depth levels of the plurality of predetermined sleep patterns matching drowsiness levels exceeding the predetermined drowsiness level being a maximum sleep depth level; and
executing a first sleep control with the electronic control unit, in which the electronic control unit maintains a sleep depth level of the individual person at the predetermined sleep depth level below the maximum sleep depth level for the target sleep time, if the drowsiness level is equal to or below the predetermined threshold;
wherein the sleep depth level is the sleep depth of the individual person being asleep.

28. A method of controlling a sleep control device, comprising:
providing the sleep control device having an electronic control unit;
providing a stimulus application device controlled by the section electronic control unit;
determining a current sleep depth level of an individual person with the electronic control unit using physiological information from a sensor;

selecting one of a plurality of predetermined sleep patterns stored in the electronic control unit with a detected drowsiness level of the individual person with the electronic control unit;

comparing the current sleep depth level with a target sleep depth level to determine whether the current sleep depth level reaches the target sleep depth level; and applying a sensory threshold stimulus from the stimulus application device to the individual person to control the current sleep depth level to maintain the target sleep depth level for a target sleep time, wherein the sensory threshold stimulus includes an intensity defined based on a human sensory threshold.

* * * * *